United States Patent
Yoon et al.

(10) Patent No.: US 11,767,311 B2
(45) Date of Patent: Sep. 26, 2023

(54) ACID SECRETION INHIBITOR AND USE THEREOF

(71) Applicant: Ildong Pharmaceutical Co., Ltd., Seoul (KR)

(72) Inventors: Hong Chul Yoon, Gyeonggi-do (KR); Joon Tae Park, Gyeonggi-do (KR); Jung Woo Lee, Gyeonggi-do (KR); Kyung Mi An, Gyeonggi-do (KR); Rang A Im, Gyeonggi-do (KR); Woo Jin Jeon, Gyeonggi-do (KR); Jae Ho Heo, Gyeonggi-do (KR); Chang Hee Hong, Gyeonggi-do (KR); Jung Eun Park, Gyeonggi-do (KR); Te Ik Sohn, Gyeonggi-do (KR); Da Hae Hong, Gyeonggi-do (KR); Jung Ho Kim, Gyeonggi-do (KR); Jae Eui Shin, Gyeonggi-do (KR); Yeong Ran Yoo, Gyeonggi-do (KR); Min Whan Chang, Gyeonggi-do (KR); In Gyu Je, Gyeonggi-do (KR); Su Yeon Kang, Gyeonggi-do (KR); Yoon Sung Song, Gyeonggi-do (KR); Joo Yun Lee, Gyeonggi-do (KR)

(73) Assignee: ILDONG PHARMACEUTICAL CO., LTD., Seoul (KR)

( * ) Notice: Subject to any disclaimer, the term of this patent is extended or adjusted under 35 U.S.C. 154(b) by 0 days.

(21) Appl. No.: 18/011,084

(22) PCT Filed: Jun. 16, 2021

(86) PCT No.: PCT/KR2021/007572
§ 371 (c)(1),
(2) Date: Dec. 16, 2022

(87) PCT Pub. No.: WO2021/256861
PCT Pub. Date: Dec. 23, 2021

(65) Prior Publication Data
US 2023/0192650 A1 Jun. 22, 2023

(30) Foreign Application Priority Data
Jun. 17, 2020 (KR) .................... 10-2020-0073900

(51) Int. Cl.
*C07D 401/12* (2006.01)
*A61P 1/04* (2006.01)
*A61P 29/00* (2006.01)

(52) U.S. Cl.
CPC .............. *C07D 401/12* (2013.01); *A61P 1/04* (2018.01); *A61P 29/00* (2018.01)

(58) Field of Classification Search
None
See application file for complete search history.

(56) References Cited

U.S. PATENT DOCUMENTS

| 2011/0288040 A1 | 11/2011 | Hasuoka et al. |
| 2016/0009646 A1 | 1/2016 | Majima |

FOREIGN PATENT DOCUMENTS

| KR | 101178747 B1 | 9/2012 |
| KR | 101613245 B1 | 4/2016 |
| KR | 1020160127646 A | 11/2016 |
| KR | 1020170113040 A | 10/2017 |
| KR | 102432523 B1 | 8/2022 |
| WO | 2019013310 A1 | 1/2019 |

OTHER PUBLICATIONS

International Search Report for corresponding PCT Application No. PCT/KR2021/007572 dated Sep. 16, 2021.
Arikawa, Y., et al. Discovery of a novel pyrrole derivative I-[5-(2-fluorophenyl)-I-(pyridin-3-ylsulfonyl)-I H-pyrrol-3-yl]-Nmethylmethanamine fumarate (TAK-438) as a potassium-competitive acid blocker (P-CAB). Journal of Medicinal Chemistry. 2012, vol. 55, pp. 4446-4456.
Korean Office Action for corresponding KR Application No. 10-2021-0078283 dated Feb. 22, 2022.
Korean Written Decision for corresponding KR Application No. 10-2021-0078283 dated Jul. 14, 2022.

*Primary Examiner* — Jeffrey S Lundgren
*Assistant Examiner* — Michael J Schmitt
(74) *Attorney, Agent, or Firm* — WOOD PHILLIPS KATZ CLARK & MORTIMER

(57) ABSTRACT

The present invention provides a novel compound represented by Chemical Formula 2, or a pharmaceutically acceptable salt thereof. The novel compound according to the present invention exhibits an excellent acid secretion inhibitory effect.

9 Claims, No Drawings

ACID SECRETION INHIBITOR AND USE THEREOF

TECHNICAL FIELD

The present disclosure relates to a novel acid secretion inhibitor and use thereof.

BACKGROUND ART

A proton pump inhibitor (PPI), represented by omeprazole that inhibits gastric acid secretion, is widely used in a clinical situation. However, the existing PPIs are accompanied by problems in view of effectiveness and side effects. Specifically, the existing PPIs are often formulated as enteric agents due to their instability under acidic conditions, and in this case, several hours are required before the onset of action, and about 5 days are required until the maximum effect is exerted by continuous administration. In addition, since the existing PPIs exhibit deviations in therapeutic effects due to metabolic enzyme polymorphisms and drug interactions with medicines such as diazepam, and the like, the drug improvement is desired.

Further, since PPIs are prodrugs activated by gastric acid and act only on the active proton pump, there are disadvantages, such as a delay in maximal drug effect expression time, ineffectiveness in suppressing acid secretion at night, the need to be taken before meals, and the like. Moreover, PPIs are mainly metabolized through the CYP2C19 enzyme, which causes a large difference in efficacy between individuals due to the gene polymorphism of the CYP2C19 enzyme.

In order to improve the above-described disadvantages of PPIs, potassium-competitive acid blockers (P-CABs) are attracting attention. The P-CABs strongly and rapidly inhibit gastric acid secretion by reversibly and competitively binding with $K^+$ ions in the proton pump ($H^+/K^+$-ATPase) which is an enzyme involved in the final stage of gastric acid secretion in gastric cells. These P-CAB formulations show strong inhibition in the normal gastric acidity (pH 1-3) compared to the PPI formulations. Meanwhile, these P-CAB formulations are required to have a pharmacological activity that decreases inhibition ability as the pH increases, but some P-CAB preparations have been reported to show a pharmacological activity that is maintained even when the pH increases, causing some side effects related to this problem. In addition, since P-CAB formulations are mainly metabolized through the CYP3A4 enzyme, the difference in efficacy between individuals is relatively small, and concerns about interactions with drugs metabolized by the CYP2C19 enzyme are relatively low.

International Patent Publication No. WO2019/013310 A1 discloses vonoprazan as the potassium-competitive acid blocker.

However, it was confirmed that vonoprazan caused severe hypergastrinemia compared to the existing PPI drug lansoprazole. Such hypergastrinemia may cause problems such as enterochromaffin-like (ECL)-cell hyperplasia; parietal cell hyperplasia; fundic gland polyp; bone loss, damaged bone quality, fractures, and the like. In fact, it has been reported that vonoprazan is associated with the development of gastric neuroendocrine tumors in carcinogenicity tests in mice and rats. However, since discontinuation of administration of P-CAB or PPI-based drugs such as vonoprazan restores gastric acid excess and causes indigestion, and the like, drug administration cannot be easily stopped in spite of the above-described problems.

On the other hand, PPIs are used for the prevention of gastric and duodenal ulcers by administration of nonsteroidal anti-inflammatory drugs (NSAIDs). However, it has been reported that vonoprazan exacerbates the damage to the small intestine caused by various types of NSAIDs. For example, NSAID-induced gastrointestinal damage includes edema, erythema, submucosal hemorrhage, erosion, ulcer, and the like, and patients who have continuously used NSAIDs for a long time have problems such as multiple small intestinal mucosal lesions, and the like. From this point of view, clinically, vonoprazan may have significant limitations in combination with NSAID drugs.

As a mechanism by which drugs such as NSAIDs or alcohols cause damage to the gastrointestinal mucosa, two major mechanisms are known: a local irritant effect and a systemic irritant effect. The local irritant effect is caused by ion-trap, mitochondrial damage, and the systemic irritant effect is caused by decrease of prostaglandin and NO (nitric oxide). In addition to mitochondrial damage caused by oxidative stress, when damage to vascular endothelial cells is applied, microcirculation is impaired, which makes the gastrointestinal mucosa very vulnerable to damage and interferes with the mucosal damage recovery mechanism. Due to the complex action of these mechanisms, damage to the gastrointestinal mucosa, i.e., gastric ulcer, enteropathy, and the like, may occur or become severe.

Accordingly, even considering the effect of vonoprazan in view of suppressing gastric acid secretion, the use of the drug is inevitably very limited due to the above-described potential problems.

Separately, *Helicobacter pylori* (*H. pylori*) is known as one of the main causes of gastrointestinal diseases such as chronic gastritis, peptic ulcer, gastric cancer, and the like. Even though the prevalence of *Helicobacter pylori* in Korea is gradually decreasing, the prevalence of 50% or more has been still reported. In particular, *Helicobacter pylori* is related to gastrointestinal diseases, and thus the importance of antibacterial treatment agents is increasing day by day. Particularly, as reported in several studies, antibacterial treatment of *Helicobacter pylori* reduces the occurrence of bleeding in peptic ulcer, and thus several countries are recommending the antibacterial treatment in these patient groups. For this antibacterial therapy, in general, patients are suggested to take clarithromycin amoxicillin, and the like, as the first-line treatment, along with gastric acid inhibitors such as PPIs. For multi-drug use of PPIs and antibiotics, the risk of drug-drug interaction (DDI) should be low, and the risk of interaction may be predicted through in vitro CYP inhibition, CYP/UGT phenotyping, CYP induction tests, and the like.

However, additional, or repeated administration of various antibiotics is required up to the second and third treatment, and side effects and tolerance due to this have been reported. Therefore, there is a need to develop a drug that reduces gastric acidity to enhance the antibacterial effect of antibiotics against *Helicobacter pylori* (*H. pylori*) and is able to be taken for a long time, for example, a drug that shows proton-potassium pump inhibition ability and the like, and antibacterial activities in various *Helicobacter pylori* strains.

In addition, in the case of an oral drug, the bioavailability, which is the rate at which the administered drug enters the systemic circulatory system and is used in the body, is measured. The higher the bioavailability, the higher the rate and extent to which the active ingredient or part of the drug is absorbed and used at the site of action, and thus high bioavailability is one of the essential elements of oral drugs.

In general, such bioavailability increases as absorption through the gastrointestinal tract is higher and the degree of first-pass effect is lower, and during administration, the bioavailability is affected by the influence of food when administering a drug, by drug interactions when taking multiple drugs, and also by drug solubility, crystal polymorphism, particle size and shape, particle surface area, and the like, from the viewpoint of drug properties.

Further, it is important to maintain the concentration of the drug in the target organ, in this case gastric tissue, as well as bioavailability in the circulatory system. Therefore, drug distribution and maintenance into the target organ, gastric tissue, are considered to be an important pharmacokinetic property in P-CAB drug development.

Meanwhile, somatostatin, also known as growth hormone-inhibiting hormone (GHIH), is a cyclic peptide expressed in the gastrointestinal tract, pancreas, hypothalamus and central nervous system. It is secreted by D cells of the stomach and pancreas and acts as a paracrine regulator of gastric acid secretion, and suppresses gastric acid secretion by inhibiting gastrin secretion by gastric G cells and acid secretion by parietal cells. Activation of somatostatin receptors by somatostatin analogs and somatostatin receptor agonists suppresses gastrin secretion to regulate histamine release from ECL cells and inhibits acid secretion. It has been reported in actual animal models and hypergastrinemia patients that the somatostatin analogue decreased the total gastric acid secretion by decreasing gastrin secretion and gastric acid response.

Suppression of gastric acid caused by taking drugs such as PPIs, and the like, induces hypergastrinemia by inhibiting somatostatin secretion by D cells and promoting gastrin secretion by G cells by a feedback mechanism. Gastrin promotes the growth of epithelial cells, induces oxyntic cell hyperplasia in the gastric body, and increases parietal cell mass. This results in proliferation of adenoma cells and hyperplasia of ECL cells, which may increase the risk of neuroendocrine tumors. In addition, the frequency of neuroendocrine tumors among tumors occurring in the duodenum is relatively high, and it is known that gastrin secretion-induced neuroendocrine tumors are the most common form of neuroendocrine tumors occurring in the duodenum, accounting for approximately 65% of the total. It was confirmed that the group treated with vonoprazan tends to have a higher gastrin level in the blood than the group treated with the existing PPI drug due to the feedback mechanism of excessive gastric acid suppression. Since hypergastrinemia may stimulate intestinal endocrine cells and may increase the risk of neuroendocrine tumors, studies on the safety of long-term use are ongoing.

Inhibition of gastrin secretion through somatostatin receptor activation has been reported to inhibit ECL cell hyperproliferation. In fact, it has been reported that synthetic peptide analogues of somatostatin with indications for endocrine diseases such as acromegaly, neuroendocrine tumors (NETs), and digestive system diseases such as upper gastrointestinal hemorrhage, and the like, i.e., Sandostatin® (octreotide acetate) and Somatuline® Depot (lanreotide), inhibit gastrin secretion in gastric neuroendocrine tumors to hinder the ECL cell hyperproliferation.

In addition, an anti-inflammatory response through somatostatin receptor activation has been reported. Somatostatin is a type of neuropeptide that inhibits neurological inflammation and regulates the secretion of hormones and neurotransmitters. It is known that somatostatin inhibits neurogenic inflammation and is involved in nociception and is also released by gastrointestinal nerve cells and neuroendocrine mucosal cells to have an anti-inflammatory action. Somatostatin is known to control the secretion of hormones and neurotransmitters to suppress neurogenic inflammation and to be involved in nociception. Inflammatory somatostatin inhibits the proliferation of T lymphocytes and granulocytes in addition to controlling the neuroendocrine system. Somatostatin analogs are known to increase the expression of the anti-inflammatory factor IL-10 and inhibit the expression of the pro-inflammatory factors IFN-$\gamma$ and TNF-$\alpha$. As a result, the anti-inflammatory role of somatostatin has been mainly reported in studies in relation to inflammatory bowel disease (IBD). It is known that intestinal somatostatin levels are reduced in patients with IBD, and it is known that the higher the level of inflammation in the intestinal tract, the lower the level of somatostatin. In fact, it has been reported that the somatostatin analogue octreotide improved the symptoms of IBD in patients and animal models.

Under this background, the present inventors synthesized a novel compound having excellent inhibitory activity on the proton pump in the present disclosure, and completed the present disclosure.

DISCLOSURE

Technical Problem

The present disclosure provides a compound represented by Chemical Formula 1 or a pharmaceutically acceptable salt thereof.

In addition, the present disclosure provides a pharmaceutical composition comprising a compound represented by Chemical Formula 1 or a pharmaceutically acceptable salt thereof.

Further, the present disclosure provides a pharmaceutical composition for preventing or treating gastrointestinal ulcers, gastrointestinal inflammatory diseases, or gastric acid-related diseases, comprising a compound represented by Chemical Formula 1 or a pharmaceutically acceptable salt thereof.

The present disclosure also provides a compound represented by Chemical Formula 1 or a pharmaceutically acceptable salt thereof for use in the prevention or treatment of gastrointestinal ulcers, gastrointestinal inflammatory diseases, or gastric acid-related diseases.

In addition, the present disclosure provides use of the compound represented by Chemical Formula 1 or the pharmaceutically acceptable salt thereof in the manufacture of a medicament for the treatment of diseases or symptoms that require prescription for acid secretion inhibitors such as gastrointestinal ulcers, gastrointestinal inflammatory diseases or gastric acid-related diseases.

Further, the present disclosure provides a method of treating gastrointestinal ulcers, gastrointestinal inflammatory diseases, or gastric acid-related diseases, comprising: administering a therapeutically effective amount of a compound represented by Chemical Formula 1 or a pharmaceutically acceptable salt thereof to a subject in need thereof.

The present disclosure also provides a gastric acid secretion inhibitor comprising the compound represented by Chemical Formula 1 or the pharmaceutically acceptable salt thereof.

Technical Solution

The present disclosure is directed to a compound represented by the following Chemical Formula 1 or a pharmaceutically acceptable salt thereof:

[Chemical Formula 1]

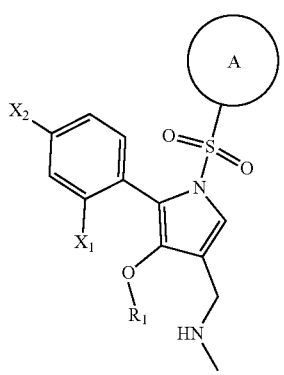

in the Chemical Formula 1,

is a substituted or unsubstituted pyridinyl group, wherein the substituted pyridinyl group is substituted with at least one or more —OH, —O($C_1$-$C_4$alkyl), —($C_1$-$C_4$alkyl), halogen, or —CN;
$X_1$ is halogen which is F, Cl, Br or I;
$X_2$ is hydrogen or halogen which is F, Cl, Br or I; and
$R_1$ is methyl or ethyl.

According to another embodiment of the present disclosure,
wherein

may be, for example, substituted or unsubstituted pyridin-3-yl, or substituted or unsubstituted pyridin-2-yl.

More specifically, wherein

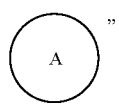

may be

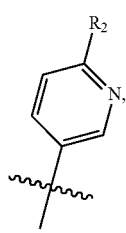

wherein $R_2$ is —O($C_1$-$C_4$alkyl) or —($C_1$-$C_4$alkyl).

According to another embodiment of the present disclosure, the compound represented by Chemical Formula 1 according to the present disclosure or the pharmaceutically acceptable salt thereof may be directed to a compound represented by the following Chemical Formula 2 or a pharmaceutically acceptable salt thereof:

[Chemical Formula 2]

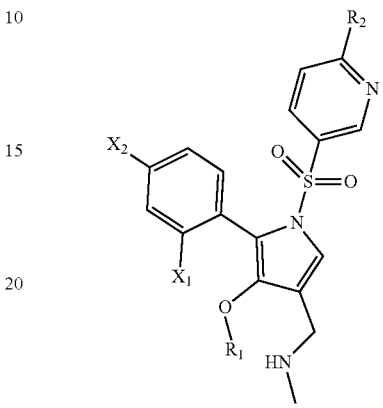

in the Chemical Formula 2,
$X_1$ is F;
$X_2$ is hydrogen or F;
$R_1$ is methyl or ethyl; and
$R_2$ is —O($C_1$-$C_4$alkyl) or —($C_1$-$C_4$alkyl).

According to another embodiment of the present disclosure,
in the Chemical Formula 2, the —O($C_1$-$C_4$alkyl) may be specifically methoxy or ethoxy. The —($C_1$-$C_4$alkyl) may be specifically methyl or ethyl.

That is, above $R_2$ may be methoxy, ethoxy, methyl or ethyl. More preferably, $R_2$ may be methoxy or methyl.

More specifically, in the Chemical Formula 2,

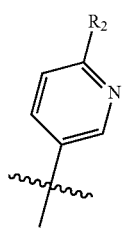

may be

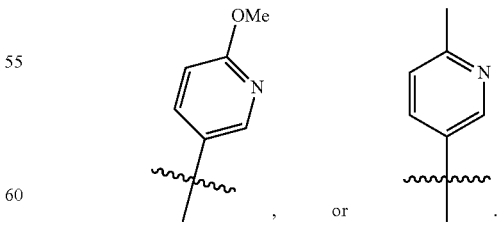

According to still another embodiment of the present disclosure, in the Chemical Formula 2, $R_1$ may be methyl.
According to still another embodiment of the present disclosure, in the Chemical Formula 2, $R_1$ may be methyl, and $R_2$ may be methoxy or methyl.

According to still another embodiment of the present disclosure, in the Chemical Formula 2, $X_1$ may be F; $X_2$ may be F; $R_1$ may be methyl; and $R_2$ may be methoxy or methyl.

According to still another embodiment of the present disclosure, in the Chemical Formula 2, $X_1$ may be F; $X_2$ may be hydrogen; $R_1$ may be methyl; and $R_2$ may be methoxy or methyl.

According to still another embodiment of the present disclosure, in the Chemical Formula 2, $X_1$ may be F; $X_2$ may be hydrogen or F; $R_1$ may be methyl; and $R_2$ may be methoxy.

According to still another embodiment of the present disclosure, in the Chemical Formula 2, $X_1$ may be F; $X_2$ may be hydrogen or F; $R_1$ may be methyl; and $R_2$ may be methyl.

Still another embodiment of the present disclosure is directed to a compound independently selected from one or any combination of the following, or a pharmaceutically acceptable salt thereof:

1-5-(2,4-difluorophenyl)-4-methoxy-1-((6-methylpyridin-2-yl) sulfonyl)-1H-pyrrol-3-yl)-N-methylmethanamine;

1-(5-(2-fluorophenyl)-4-methoxy-1-(pyridin-2-ylsulfonyl)-1H-pyrrol-3-yl)-N-methylmethanamine;

1-(5-(2-fluorophenyl)-4-methoxy-1-((6-methoxypyridin-3-yl) sulfonyl)-1H-pyrrol-3-yl)-N-methylmethanamine;

1-(5-(2,4-difluorophenyl)-4-methoxy-1-((6-methoxypyridin-3-yl)sulfonyl)-1H-pyrrol-3-yl)-N-methylmethanamine;

1-(5-(2,4-difluorophenyl)-4-methoxy-1-((6-methylpyridin-3-yl) sulfonyl)-1H-pyrrol-3-yl)-N-methylmethanamine; and 1-(5-(2-fluorophenyl)-4-methoxy-1-((6-methylpyridin-3-yl)sulfonyl)-1H-pyrrol-3-yl)-N-methylmethanamine.

Another more preferred embodiment of the present disclosure is directed to the compound represented by Chemical Formula 2 or the pharmaceutically acceptable salt thereof, and is directed a compound independently selected from one or any combination of the following, or a pharmaceutically acceptable salt thereof:

1-(5-(2-fluorophenyl)-4-methoxy-1-((6-methoxypyridin-3-yl)sulfonyl)-1H-pyrrol-3-yl)-N-methylmethanamine;

1-(5-(2,4-difluorophenyl)-4-methoxy-1-((6-methoxypyridin-3-yl)sulfonyl)-1H-pyrrol-3-yl)-N-methylmethanamine;

1-(5-(2,4-difluorophenyl)-4-methoxy-1-((6-methylpyridin-3-yl)sulfonyl)-1H-pyrrol-3-yl)-N-methylmethanamine; and 1-(5-(2-fluorophenyl)-4-methoxy-1-((6-methylpyridin-3-yl)sulfonyl)-1H-pyrrol-3-yl)-N-methylmethanamine.

Another even more preferred embodiment of the present disclosure is directed to the compound represented by Chemical Formula 2 or the pharmaceutically acceptable salt thereof, and is directed to a compound independently selected from one or any combination of the following, or a pharmaceutically acceptable salt thereof:

1-(5-(2-fluorophenyl)-4-methoxy-1-((6-methoxypyridin-3-yl)sulfonyl)-1H-pyrrol-3-yl)-N-methylmethanamine; and 1-(5-(2,4-difluorophenyl)-4-methoxy-1-((6-methylpyridin-3-yl)sulfonyl)-1H-pyrrol-3-yl)-N-methylmethanamine.

In the present disclosure, the pharmaceutically acceptable salt means a salt commonly used in the pharmaceutical industry, and for example, may be inorganic ionic salts prepared from calcium, sodium, and the like, inorganic acid salts prepared from phosphoric acid, bromic acid, iodic acid, sulfuric acid, and the like, organic acid salts prepared from acetic acid, trifluoroacetic acid, citric acid, maleic acid, lactic acid, glycolic acid, ascorbic acid, carbonic acid, vanillic acid, and the like, sulfonic acid salts prepared from methanesulfonic acid, ethanesulfonic acid, benzenesulfonic acid, and the like, amino acid salts prepared from glycine, arginine, and the like, and amine salts prepared from trimethylamine, triethylamine, and the like, but the types of salts in the present disclosure are not limited to these listed salts.

In still another embodiment of the present disclosure, there is provided a pharmaceutical composition comprising the compound represented by Chemical Formula 1 as defined in any of the embodiments described in the present disclosure, or the pharmaceutically acceptable salt thereof.

In still another embodiment of the present disclosure, there is provided a pharmaceutical composition comprising the compound represented by Chemical Formula 1 as defined in any of the embodiments described in the present disclosure, or the pharmaceutically acceptable salt thereof; and a pharmaceutically acceptable carrier.

In still another embodiment of the present disclosure, there is provided a pharmaceutical composition for preventing or treating gastrointestinal ulcers, gastrointestinal inflammatory diseases, or gastric acid-related diseases, comprising the compound represented by Chemical Formula 1 as defined in any of the embodiments described in the present disclosure, or the pharmaceutically acceptable salt thereof.

The present disclosure also encompasses the following embodiments:

the compound represented by Chemical Formula 1 as defined in any of the embodiments described in the present disclosure, or the pharmaceutically acceptable salt thereof, for use as a medicament;

the compound represented by Chemical Formula 1 as defined in any of the embodiments described in the present disclosure, or the pharmaceutically acceptable salt thereof, for use in the prevention or treatment of gastrointestinal ulcers, gastrointestinal inflammatory diseases or gastric acid-related diseases discussed in the present disclosure;

a method of treating gastrointestinal ulcers, gastrointestinal inflammatory diseases, or gastric acid-related diseases, comprising: administering a therapeutically effective amount of the compound represented by Chemical Formula 1 as defined in any of the embodiments described in the present disclosure, or the pharmaceutically acceptable salt thereof to a subject in need thereof;

use of the compound represented by Chemical Formula 1 as defined in any of the embodiments described in the present disclosure, or the pharmaceutically acceptable salt thereof, in the manufacture of a medicament for the treatment of diseases or symptoms that require prescription for acid secretion inhibitors such as gastrointestinal ulcers, gastrointestinal inflammatory diseases or gastric acid-related diseases;

the compound represented by Chemical Formula 1 as defined in any of the embodiments described in the present disclosure, or the pharmaceutically acceptable salt thereof, for use in the treatment of diseases or symptoms that require prescription for acid secretion inhibitors;

a pharmaceutical composition comprising the compound represented by Chemical Formula 1 as defined in any of the embodiments described in the present disclosure, or the pharmaceutically acceptable salt thereof, for the treatment of diseases or symptoms that require prescription for acid secretion inhibitors; or a gastric acid secretion inhibitor comprising the compound represented by Chemical Formula 1 as defined in any of the embodiments described in the present disclosure, or the pharmaceutically acceptable salt thereof.

The above-described compound represented by Chemical Formula 1 or a pharmaceutically acceptable salt thereof is preferably a compound represented by Chemical Formula 2 or a pharmaceutically acceptable salt thereof.

All of the Examples or pharmaceutically acceptable salts thereof may be claimed individually or as a group together in any combination with any number of each and every embodiment described herein.

The present disclosure is also directed to a pharmaceutical composition comprising the compound represented by Chemical Formula 1 as defined in any of the embodiments described in the present disclosure, or a pharmaceutically acceptable salt thereof, for use in the prevention or treatment of gastrointestinal ulcers, gastrointestinal inflammatory diseases or gastric acid-related diseases as discussed herein.

Specifically, the gastrointestinal ulcer refers to an ulcer that occurs in the digestive system including both the stomach and intestines. Examples of the gastrointestinal ulcer may include, but are not limited to, peptic ulcer, gastric ulcer, duodenal ulcer, NSAID-induced ulcer, acute stress ulcer, Zollinger-Ellison syndrome, and the like. If the ulcer becomes serious, cancer may be developed. For example, the gastric ulcer may develop into gastric cancer as the severity of disease increases.

In particular, the gastrointestinal ulcer may include damage to the gastric mucosa or damage to the small intestinal mucosa caused by drugs, alcohol, or the like. In particular, it may be damage to the gastric mucosa or damage to the small intestinal mucosa caused by NSAIDs or alcohol.

The gastrointestinal inflammatory disease refers to a disease caused by inflammation of the gastrointestinal tract.

The gastrointestinal inflammatory disease includes, for example, but is not limited to, *Helicobacter pylori* infection, gastritis (for example, acute hemorrhagic gastritis, chronic superficial gastritis, chronic atrophic gastritis), inflammatory bowel disease, gastric MALT lymphoma, and the like.

The gastric acid-related disease refers to a disease caused by excessive secretion of gastric acid. For example, the gastric acid-related disease includes, but is not limited to, erosive esophagitis, non-erosive esophagitis, reflux esophagitis, symptomatic gastroesophageal reflux disease (symptomatic GERD), functional dyspepsia, hyperacidity, upper gastrointestinal hemorrhage due to invasive stress, and the like.

According to the present disclosure, the gastrointestinal ulcer, gastrointestinal inflammatory disease or gastric acid-related disease may be any one or more select from the group consisting of peptic ulcer, gastric ulcer, duodenal ulcer, NSAID-induced ulcer, acute stress ulcer, Zollinger-Ellison syndrome, *Helicobacter pylori* infection, gastritis, erosive esophagitis, non-erosive esophagitis, reflux esophagitis, inflammatory bowel disease, symptomatic gastroesophageal reflux disease (symptomatic GERD), functional dyspepsia, gastric cancer, gastric MALT lymphoma, hyperacidity, and upper gastrointestinal upper gastrointestinal hemorrhage due to invasive stress.

The compound represented by Chemical Formula 2 according to the present disclosure or the pharmaceutically acceptable salt thereof directly and reversibly inhibits the proton pump to exhibit a rapid pharmacological effect and low drug interaction, thereby showing an excellent effect in pharmacological safety. In detail, in terms of safety, the compound represented by Chemical Formula 2 or the pharmaceutically acceptable salt thereof does not inhibit the CYP enzyme, which is a major liver metabolizing enzyme, and thus it is judged to be less likely to exhibit drug-drug interaction.

The compound represented by Chemical Formula 2 according to the present disclosure or the pharmaceutically acceptable salt thereof may have a high intragastric distribution to be maintained in high concentrations in the stomach, thereby allowing adequate control of long-term gastric acid activity, and thus it has advantages in that it exhibits an excellent effect even in view of inhibiting acid secretion at night and has fluidity even at the time of administration. Further, the compound represented by Chemical Formula 2 according to the present disclosure or the pharmaceutically acceptable salt thereof exhibits high bioavailability in the oral route of administration, thereby showing a very good effect in view of pharmacokinetics. In other words, the compound represented by Chemical Formula 2 according to the present disclosure or the pharmaceutically acceptable salt thereof may have excellent bioavailability upon oral administration together with excellent intragastric distribution, thereby showing exhibiting a sufficiently excellent effect of inhibiting gastric acid secretion even with a small amount of the drug. In particular, the concentration of the drug in the stomach is maintained above an appropriate level and shows sufficient efficacy while showing an excellent effect without the risk of indigestion, abdominal pain, hypergastrinemia, and the like, due to excessive compensatory action.

In particular, the compound represented by Chemical Formula 2 according to the present disclosure or the pharmaceutically acceptable salt thereof exhibits excellent somatostatin receptor agonist activity. Accordingly, acid secretion may be controlled without the risk of hypergastrinemia by effectively inhibiting gastrin secretion. In addition, the risk of hypergastrinemia may be minimized by regulating the concentration of gastrin in the blood. In particular, excellent efficacy is shown in regulating acid secretion without side effects or problems such as hyperplasia and neuroendocrine tumors that may be caused by hypergastrinemia, and the like.

The compound represented by Chemical Formula 2 according to the present disclosure or the pharmaceutically acceptable salt thereof exhibits excellent effects of reversibly (at an appropriate pH) restoring the enzymatic activity of the proton pump while simultaneously showing inhibition ability by acting on the proton pump within a short time at low pH.

The compound represented by Chemical Formula 2 according to the present disclosure or the pharmaceutically acceptable salt thereof has excellent therapeutic effect on gastrointestinal damage including gastrointestinal ulcers and gastrointestinal inflammatory diseases occurring by causes other than gastric acid, thanks to excellent somatostatin receptor agonist activity. For example, excellent effects of improving inflammation and improving gastric mucosa in the gastric mucosa damage or intestinal mucosa damage induced by the drug. Specifically, it is possible to exhibit an excellent effect of improving the mucous membrane of the gastrointestinal tract against NSAID-induced gastrointestinal damage and gastrointestinal inflammatory diseases, alcohol-induced gastrointestinal damage and gastrointestinal inflammatory diseases. In addition, it is possible to exhibit an excellent effect in disease treatment by remarkably improving the inflammatory cytokine and ROS levels with respect to NSAID-induced gastrointestinal damage and gastrointestinal inflammatory diseases, and alcohol-induced gastrointestinal damage and gastrointestinal inflammatory diseases.

In particular, the compound represented by Chemical Formula 2 according to the present disclosure or the pharmaceutically acceptable salt thereof exhibits excellent therapeutic efficacy against gastrointestinal ulcers and gastrointestinal inflammatory diseases through excellent somatostatin receptor agonist activity. In detail, an excellent effect in the treatment of diseases may be exhibited by minimizing the ulcer lesion and remarkably improving the inflammatory cytokine and ROS levels with respect to esophagitis ulcers or duodenal ulcers.

In particular, the compound represented by Chemical Formula 2 according to the present disclosure or the pharmaceutically acceptable salt thereof may have a therapeutic effect without deterioration of small intestine damage induced by drugs such as NSAIDs, unlike existing P-CAB drugs, through excellent somatostatin receptor agonist activity, and thus the therapeutic efficacy for intestinal diseases, including inflammatory bowel disease (IBD), may be exhibited together with increasing the category of patient groups for which the drug is able to be used.

The compound represented by Chemical Formula 2 according to the present disclosure or the pharmaceutically acceptable salt thereof is useful for the prevention and treatment of digestive diseases such as chronic gastritis, peptic ulcer, gastric cancer, and the like, caused by *Helicobacter pylori*, by reducing gastric acidity to enhance the antibacterial effect of antibiotics against *Helicobacter pylori* (*H. pylori*).

The terms and symbols used in the present disclosure are provided as follows.

PG: protecting group
DMF: dimethylformamide
EA: ethyl acetate
DCM: dichloromethane
TFA: trifluoroacetic acid
NaH: sodium hydride
NaBH$_4$: sodium borohydride
NaHCO$_3$: sodium bicarbonate
Na$_2$S$_2$O$_3$: sodium thiosulfate
Boc: Cert-butoxycarbonyl protecting group
DIBAL-H: diisobutylaluminum hydride
DMP: Dess-Martin periodinane
THF: tetrahydrofuran As used herein, the term "halogen" refers to fluoride, chloride, bromide, or iodide.

The term "alkyl" refers to a straight-chain or branched-chain hydrocarbon group of the structural formula —C$_n$H$_{(2n+1)}$ Non-limiting examples thereof include methyl, ethyl, propyl, isopropyl, butyl, 2-methyl-propyl, 1,1-dimethyl-ethyl, pentyl, hexyl, and the like. For example, "C$_1$-C$_4$ alkyl" may refer to an alkyl such as methyl, ethyl, propyl, butyl, 2-methyl-propyl, or isopropyl.

In the present disclosure, the term "alkoxy" means "—O-alkyl" or "alkyl-O—", in which the alkyl is the same as defined above.

In the present disclosure, the symbol "

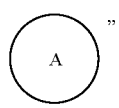

"

may be a substituted or unsubstituted pyridinyl group.

The substituted pyridinyl group is the same as defined above.

The term "pyridinyl group" as used herein refers to a 6-membered heteroaryl compound containing 1 nitrogen atom and 5 carbon atoms. Non-limiting examples of the pyridinyl group include:

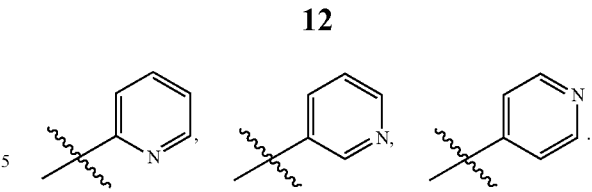

In the present disclosure, when the symbol "

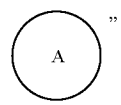

"

is substituted, specifically, when it is a substituted pyridinyl group, it may be substituted with one or two —O(C$_1$-C$_4$alkyl) or —(C$_1$-C$_4$alkyl). The —O(C$_1$-C$_4$alkyl) may be specifically methoxy or ethoxy. The —(C$_1$-C$_4$alkyl) may be specifically methyl or ethyl.

More preferably, the substituted pyridinyl group may be

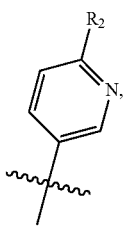

wherein R$_2$ is —O(C$_1$-C$_4$alkyl) or —(C$_1$-C$_4$alkyl).

The —O(C$_1$-C$_4$alkyl) may be specifically methoxy or ethoxy.

The —(C$_1$-C$_4$alkyl) may be specifically methyl or ethyl.

For example, when the symbol"

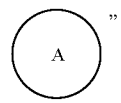

"

is substituted in the present disclosure, non-limiting examples thereof include:

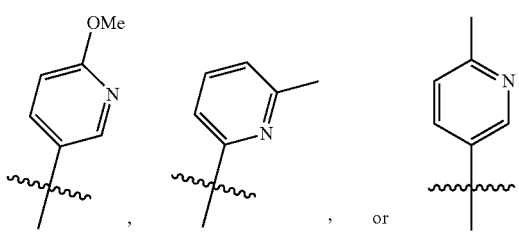

In the present disclosure, when the symbol "

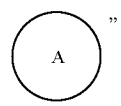

"

is unsubstituted, non-limiting examples thereof include: pyridin-3-yl, or pyridin-2-yl.

In another embodiment, the present disclosure includes a pharmaceutical composition.

The present disclosure provides a pharmaceutical composition for preventing and treating gastrointestinal ulcers, gastrointestinal inflammatory diseases, or gastric acid-related diseases, comprising the compound represented by Chemical Formula 1 or the pharmaceutically acceptable salt thereof.

The pharmaceutical composition may include the compound of the present disclosure together with a pharmaceutically acceptable carrier. Other pharmacologically active ingredients may also be present. The "pharmaceutically acceptable carrier" in the present disclosure includes any and all solvents, dispersion media, coatings, antibacterial and antifungal agents, isotonic agents, absorption retarders, and the like, that are physiologically compatible.

The composition of the present disclosure may be in various forms. The composition includes, for example, liquid, semi-solid and solid dosage forms, such as liquid solutions (for example, injectable and infusible solutions), dispersions or suspensions, tablets, pills, powders, liposomes and suppositories. The form depends on the intended mode of administration and the therapeutic use.

A typical composition is in the form of compositions similar to injectable and infusible solutions. One mode of administration is parenteral (for example, intravenous, subcutaneous, intraperitoneal, intramuscular).

Oral administration of solid dosage forms may be provided, for example, as hard or soft capsules, pills, sachets, lozenges or tablets, each containing a predetermined amount of one or more compounds of the present disclosure. In another embodiment, the oral administration may be provided in a powder or granular form.

In still another embodiment, the oral administration may be provided in a liquid dosage form. The liquid dosage form for oral administration includes, for example, pharmaceutically acceptable emulsions, solutions, suspensions, syrups, and elixirs containing an inert diluent (for example, water) commonly used in the art.

In still another embodiment, the present disclosure encompasses a parenteral dosage form. The "parenteral administration" includes, for example, subcutaneous injection, intravenous injection, intraperitoneal injection, intramuscular injection, intrasternal injection, and infusion. Injectable preparations (i.e., sterile injectable aqueous or oleaginous suspensions) may be formulated according to known techniques using suitable dispersants, wetting and/or suspending agents.

Other carrier materials and administration modes known in the pharmaceutical art may also be employed. The pharmaceutical compositions of the present disclosure may be prepared by any of the well known pharmaceutical techniques, such as effective formulation and administration procedures.

Typically, the compound of the present disclosure is administered in an amount effective to treat the symptoms described in the present disclosure. The compound of the present disclosure may be administered as the compound as it is, or alternatively, as a pharmaceutically acceptable salt. For administration and dosage purposes, the compound as it is, or a pharmaceutically acceptable salt thereof, will be referred to simply as the compound of the present disclosure.

The compound of the present disclosure is administered by any suitable route, in the form of a pharmaceutical composition suitable for the route, and in a dosage effective for the intended treatment. The compound of the present disclosure may be administered orally, rectally, intravaginally, parenterally, or topically.

The compound of the present disclosure may preferably be administered orally. The oral administration may involve swallowing the compound to enter the gastrointestinal tract.

In another embodiment, the compound of the present disclosure may also be administered directly into the blood flow, muscle, or internal organs. Suitable means for parenteral administration include intravenous, intraarterial, intraperitoneal, intramuscular and subcutaneous administration.

The dosing regimen of the compound of the present disclosure and/or the composition containing the compound will depend on various factors including the patient's type, age, weight, gender and medical condition; severity of symptoms; route of administration; and the activity of the particular compound employed. Accordingly, the dosing regimen may vary widely. In an embodiment, the total daily dosage of the compound of the present disclosure is typically from about 0.001 to about 100 mg/kg [i.e., expressed in the compound of the present disclosure (mg) per body weight (kg)] for treatment of the indicated symptoms discussed in the present disclosure.

Suitable subjects according to the present disclosure include mammalian subjects. In an embodiment, a human is a suitable subject. The human subject may be male or female and at any stage of growth.

Preparation

The Reaction Schemes to be described below are intended to provide a general description of the methodology used for the preparation of the compounds of the present disclosure.

The compound represented by Chemical Formula 1 of the present disclosure includes compounds of Examples to be prepared below. The compounds of Examples are prepared or may be prepared with reference to various methods described in the document and common general technical knowledge known to those skilled in the art on the basis of intermediate compounds. The compounds of Examples are prepared or may be prepared with reference to the following route of Reaction Scheme 1 or Scheme 2 described in the document or the common general technical knowledge known to those skilled in the art on the basis of intermediate compounds.

The Reaction Schemes 1 and 2 to be described below disclose a method of preparing the Chemical Formula 1 through an intermediate. The Reaction Scheme 3 to be described below discloses a method of preparing an intermediate (I) used in the Reaction Scheme 1. The Reaction Scheme 4 to be described below discloses a method of preparing an intermediate (VI) used in the Reaction Scheme 2.

Synthetic Route

1. Synthetic Route (1) of Compound of Chemical Formula 1

[Reaction Scheme 1]

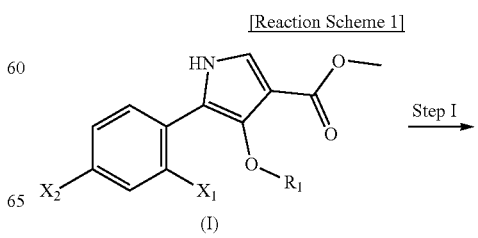

-continued

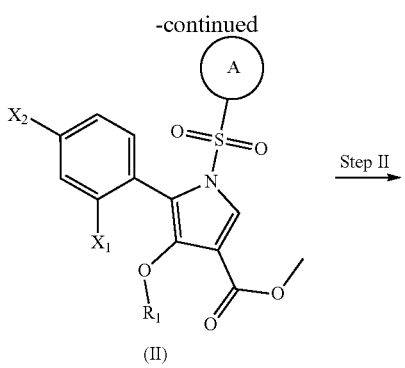

(II)

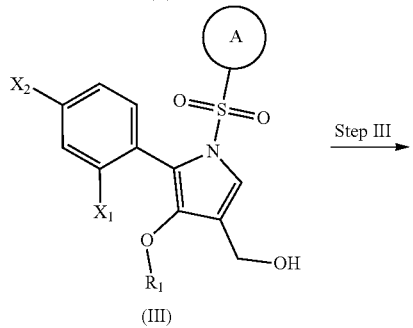

(III)

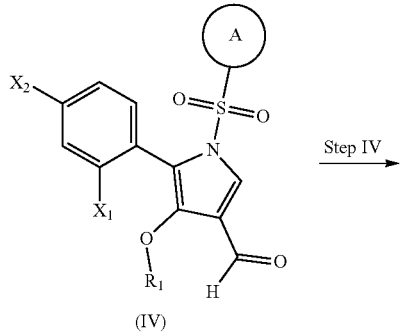

(IV)

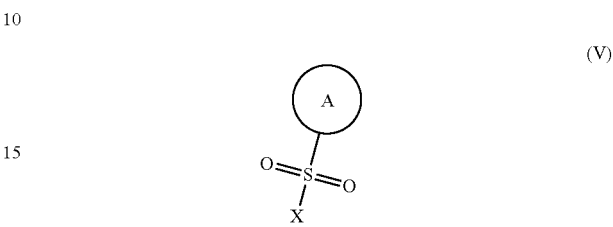

Chemical Formula I (1) Reaction of Step (I)

Intermediate (II) may be prepared through the reaction shown in Step (I) employing Intermediate (I) and Intermediate (V) to be described below. The present reaction is a process for introducing an appropriate heteroarylsulfonyl group using a base in the presence of an inert solvent. The solvent used in the reaction of Step (I) is preferably hydrocarbons such as toluene and benzene, ethers such as tetrahydrofuran and diethyl ether, N,N-dimethylformamide, or a mixed solvent thereof, and the like, but is not limited thereto. The base used in the present reaction is preferably an inorganic salt such as sodium hydroxide, a basic salt such as cesium carbonate, or a metallic salt such as sodium methoxide, and the like, but is not limited thereto. The preferred reaction time of the present reaction varies depending on the compound, but is generally from 10 minutes to 16 hours. The preferred reaction temperature for the present reaction varies depending on the compound, but is generally 0° C. to 140° C. The reaction may be performed under the addition of crown ether in order for the present reaction to proceed properly, and examples of the crown ether include 15-crown-5-ether, and the like.

(V)

Intermediate (V) is a substance that is commercially available or is able to be prepared through a generally well-known method, and ring A of the Intermediate (V) is the same as defined in Chemical Formula 1 above. The symbol "X" of the intermediate (V) means a halogen element, for example, a halogen element such as F, Cl, Br, or the like.

(2) Reaction of Step (II)

Intermediate (III) may be prepared from Intermediate (II) through the reaction represented by Step (II). The step (II) reaction is a process of reduction using a reducing agent in the presence of an inert solvent. The solvent used in the present reaction is preferably hydrocarbons such as toluene and benzene, ethers such as tetrahydrofuran and diethyl ether, or a mixed solvent thereof, and the like, but is not limited thereto. The reducing agent used in the present reaction is preferably diisobutylaluminum hydride, lithium aluminumhydride, and the like, but is not limited thereto. The preferred reaction time of the present reaction varies depending on the compound, but is preferably 10 minutes to 6 hours. The preferred reaction temperature for the present reaction varies depending on the compound, but is preferably −78° C. to 25° C.

(3) Reaction of Step (III)

Intermediate (IV) may be prepared from Intermediate (III) through the reaction represented by Step (III). The reaction of Step (III) is a process of oxidation using an oxidizing agent in the presence of an inert solvent. The solvent used in the present reaction is preferably an organic halogen solvent such as dichloromethane or a mixed solvent thereof, and the like, but is not limited thereto. The oxidizing agent used in the present reaction is preferably Dess-Martin periodinane, pyridium chlorochromate, and the like, but is not limited thereto. The preferred reaction time of the present reaction varies depending on the compound, but is preferably 10 minutes to 6 hours. The preferred reaction temperature for the present reaction varies depending on the compound, but is preferably 0° C. to 25° C.

(4) Reaction of Step (IV)

The compound of Chemical Formula (1) may be prepared from the intermediate (IV) through the reaction represented by Step (IV). The reaction of Step (IV) is a reductive amination process using an appropriate amine and a reducing agent. The solvent used in the present reaction is preferably ethers such as tetrahydrofuran and diethyl ether, alcohols such as methanol and ethanol, or a mixed solvent thereof, and the like, but is not limited thereto. The present reaction is terminated by performing a reaction with a suitable amine such as methylamine, or the like, for an appropriate time to form an imine, and adding a suitable reducing agent. The reducing agent used in the present reaction is preferably sodium borohydride, sodium cyanoborohydride, or sodium triacetoxyborohydride, and the like, but is not limited thereto. The preferred reaction time of the present reaction varies depending on the compound, but is preferably 1 hour to 6 hours. The preferred reaction temperature of the present reaction varies depending on the compound, but is preferably 0° C. to 60° C.

2. Synthetic Route (2) of Compound of Chemical Formula 1

The compound of [Chemical Formula 1] may also be prepared by the method of Reaction Scheme 2 below:

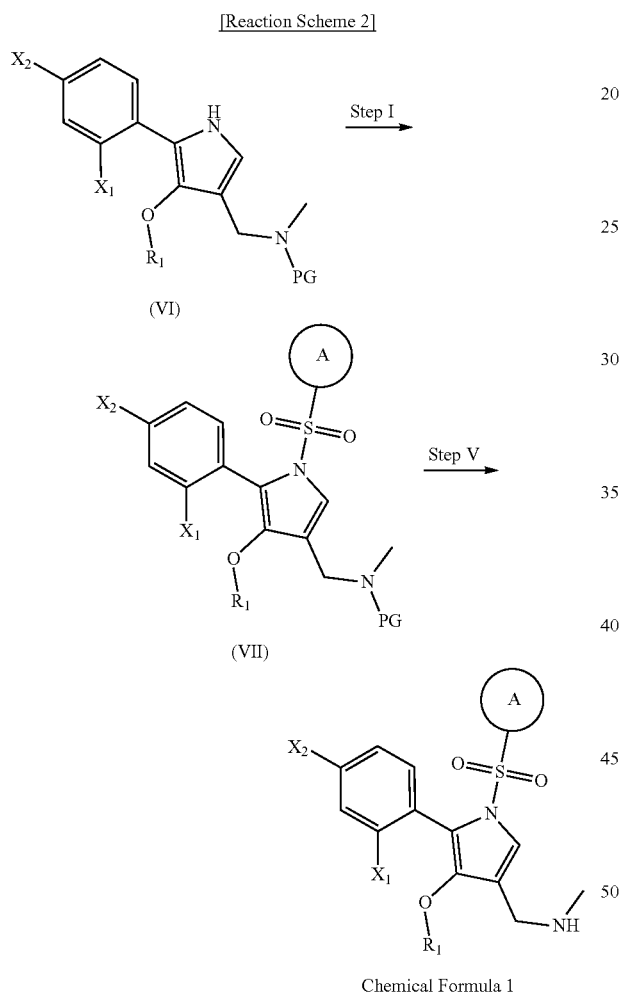

(1) Reaction of Step (I)

Intermediate (VII) may be prepared from Intermediate (VI) according to the same or similar method to the preparation method of Step (I) of the Reaction Scheme 1 above.

(2) Reaction of Step (V)

The compound of Chemical Formula 1 may be prepared from the intermediate (VII) through the reaction represented by Step (V). The reaction of Step (V) is a deprotection process that removes the protecting group under suitable conditions. The deprotection reaction is not limited to specific acid or base conditions, for example, hydrogen chloride-1,4-dioxane solution, trifluoroacetic acid-dichloromethane, potassium carbonate-methanol solution, and the like, may be used, but the substance to be used is not limited thereto. The preferred reaction time of the present reaction varies depending on the compound, but is preferably 10 minutes to 6 hours. The preferred reaction temperature for the present reaction varies depending on the compound, but is preferably 0° C. to 25° C.

3. Synthetic Route of Intermediate (I) of Reaction Scheme 1

Intermediate (I) of Reaction Scheme 1 above may be prepared as in Reaction Scheme 3 below.

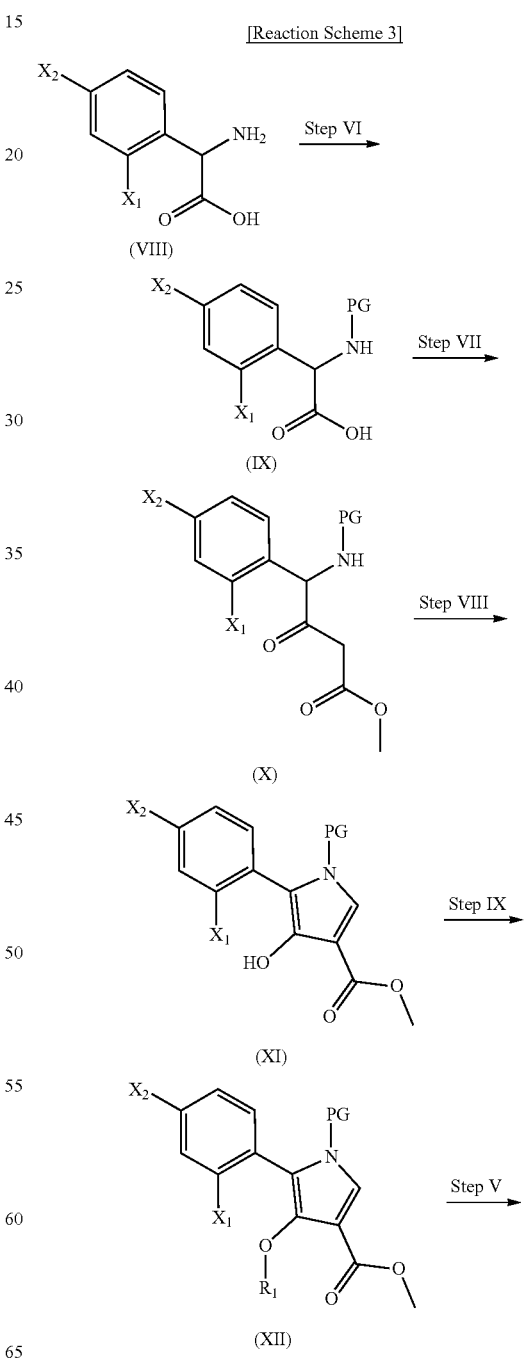

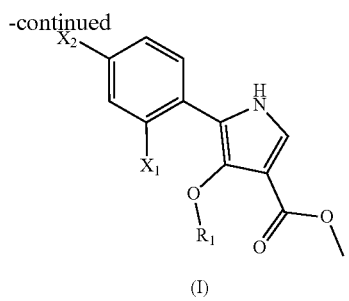

(I)

(1) Reaction of Step (VI)

Intermediate (IX) may be prepared from intermediate (VIII) through the reaction represented by Step (VI). The reaction of Step (VI) is a process for introducing a protecting group to the amine group of intermediate (VIII). The reaction of introducing a protecting group may be performed according to, for example, well-known methods such as several methods suggested by T. W. Green (see Protective Groups in Organic Synthesis, 4th Ed. 2007, Wiely & Sons).

(2) Reaction of Step (VII)

Intermediate (X) may be prepared from intermediate (IX) through the reaction represented by Step (VII). Step (VII) reaction is the Claisen condensation reaction for synthesizing beta-ketoesters from carboxylic acids. It is a reaction of performing activation via an appropriate leaving group such as carbonyldiimidazole, and the like, followed by condensation via Turbo Grignard such as magnesium chloride, or the like, followed by decarboxylation at an appropriate acidity, for example, under acidic conditions. The solvent used in the present reaction is preferably ethers such as tetrahydrofuran and diethyl ether, or a mixed solvent thereof, and the like, but is not limited thereto. The reaction varies depending on the compound, but is preferably from 3 hours to 24 hours at room temperature, but is not limited thereto.

(3) Reaction of Step (VIII)

Intermediate (XI) may be prepared from intermediate (X) through the reaction represented by Step (VIII). Step (VIII) reaction is a pyrrole cyclization reaction that proceeds under appropriate conditions. The cyclization is a reaction in which the beta-ketoester substrate produces an activated methylene group and nucleophilic attack of nitrogen in the molecule allows cyclization to proceed, in the presence of N,N-dimethylformamide dimethyl acetal. The solvent used in the present reaction is preferably hydrocarbons such as toluene and benzene, ethers such as 1,4-dioxane, or a mixed solvent thereof, and the like, but is not limited thereto. The preferred reaction time of the present reaction varies depending on the compound, but is preferably 2 hours to 12 hours. The preferred reaction temperature of the present reaction varies depending on the compound, but is preferably 40° C. or higher, and in some cases 100° C. or higher.

(4) Reaction of Step (IX)

Intermediate (XII) may be prepared from intermediate (XI) through the reaction represented by Step (IX). Step (IX) reaction is an alkylation reaction of the hydroxyl group in a compound. The solvent used in the present reaction is preferably ethers such as tetrahydrofuran and diethyl ether, alcohols such as methanol and ethanol, N,N-dimethylformamide, or a mixed solvent thereof, and the like, but is not limited thereto. The alkylation may be performed in the presence of an appropriate base, for example, by reacting with diethyl sulfate, dimethyl sulfate, or the like, in potassium carbonate, or the like, or by employing an alkylating agent such as trimethylsilyl diazomethane, or the like. The preferred reaction time of the present reaction varies depending on the compound, but is preferably 3 hours to 24 hours. The preferred reaction temperature of the present reaction varies depending on the compound, but is preferably 0° C. to 50° C.

(5) Reaction of Step (V)

Intermediate (I) may be prepared from Intermediate (XII) according to the same or similar method to the preparation method of Step (V) of the Reaction Scheme 2 above.

4. Synthetic Route of Intermediate (VI) of Reaction Scheme 2

The compound of the intermediate (VI) of Reaction Scheme 2 above may be prepared as in Reaction Scheme 4 below.

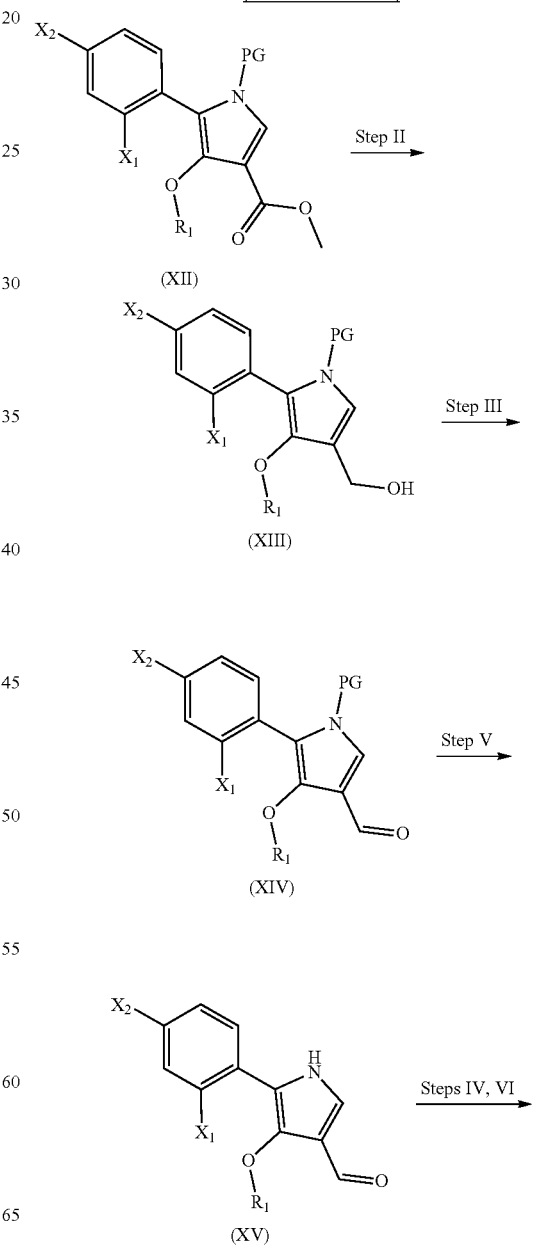

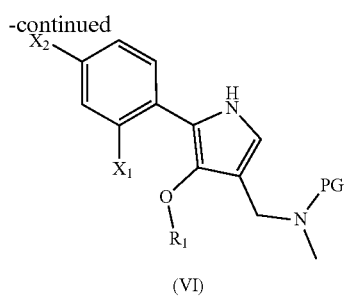

(VI)

(1) Reaction of Step (II)

Intermediate (XIII) may be prepared from Intermediate (XII) according to the same or similar method to the preparation method of Step (II) of the Reaction Scheme 1 above.

(2) Reaction of Step (III)

Intermediate (XIV) may be prepared from Intermediate (XIII) according to the same or similar method to the preparation method of Step (III) of the Reaction Scheme 1 above.

(3) Reaction of Step (V)

Intermediate (XV) may be prepared from Intermediate (XIV) according to the same or similar method to the preparation method of Step (V) of the Reaction Scheme 2 above.

(4) Reaction of Steps (IV) and (VI)

Intermediate (VI) may be prepared from Intermediate (XV) according to the same or similar method over two steps of Reaction Schemes 1 and 3, i.e., Steps (IV) and (VI).

Advantageous Effects

The novel derivative according to the present disclosure or a pharmaceutically acceptable salt thereof directly and reversibly inhibits the proton pump, thereby exhibiting rapid pharmacological effects and low drug interaction. In addition, the compound of the present disclosure may have high bioavailability to exhibit high pharmacological effects even with a small dosage, may have a high intragastric distribution, and may be maintained at an appropriate level or higher in the stomach to control gastric acid activity for a long period of time. In addition, it is useful not only for the prevention or treatment of gastrointestinal ulcers, gastrointestinal inflammatory diseases, or gastric acid-related diseases, but also for the prevention and treatment of digestive diseases such as chronic gastritis, peptic ulcer, gastric cancer, and the like, caused by *Helicobacter pylori*, by reducing gastric acidity to enhance the antibacterial effect of antibiotics against *Helicobacter pylori* (*H. pylori*). Further, the compound of the present disclosure exhibits somatostatin receptor agonist activity and suppresses gastrin secretion, thereby effectively suppressing gastric acid secretion without the risk of hypergastrinemia compared to existing PPIs.

BEST MODE

Hereinafter, preparation methods and Experimental Examples of the present disclosure will be described in detail. However, the present disclosure is not limited to these preparation methods and Examples.

Reagents and solvents described below were purchased from Sigma-Aldrich, TCI, unless otherwise noted.

The NMR measurements of all compounds were performed using a Bruker Avance™ NEO NMR spectrometer (400 MHz for $^1$H, 100 MHz for $^{13}$C). Mass spectrometry was performed using a Masslynx system and an LC/MS system based on Waters UPLC, and purity was measured by reverse-phase HPLC using a Waters e2695 system. Unless otherwise specified, HPLC analysis conditions are as follows.

[HPLC Method I]

Mobile phase A: 0.1% TFA in acetonitrile, mobile phase B: 0.1% TFA in H$_2$O

Gradient Elution Composition

Initial conditions: A: 10%, B: 90%

A: 10%, B: from 90% A: 100%, B: 0% (from t=0 min up to t=20 min)

A: 100%, B: 0% maintained (from t=20 min up to t=30 min)

A: 100%, B: from 0% A: 10%, B: 90% (from t=30 min up to t=30.10 min)

A: 10%, B: 90% maintained (from t=30.10 min up to t=40 min)

flow rate: 1.0 mL/min, injection volume: 10 μl $^1$H nuclear magnetic resonance (NMR) spectra were consistent with the proposed structure in all cases. The characteristic chemical shift (δ) is given in parts-per-million (ppm) for residual proton signal in a deuterated solvent (CDCl$_3$: 7.27 ppm; CD$_2$HOD: 3.31 ppm; DMSO-d$_6$: 2.50 ppm), and common abbreviations for designations of major peaks are reported: for example, s, singlet; d, doublet; t, triplet; q, quartet; m, multiplet; br, broadness. $^1$H NMR spectra were obtained using an electric field intensity of 400 MHz, unless otherwise noted.

Synthetic Example

Synthetic Example 1. Synthesis of Intermediates 1 to 4

[Intermediate 1] methyl 5-(2-fluorophenyl)-4-methoxy-1I-pyrrole-3-carboxylate

Step (1) Synthesis of 2-((tert-butoxycarbonyl)amino)-2-(2-fluorophenyl)acetic acid 2-Amino-2-(2-fluorophenyl)acetic acid (1.0 eq., 2.0 g, 11.82 mmol) was dissolved in THF/H$_2$O=1:1 (70 mL), and then sodium hydrogen carbonate (3.0 eq., 2.98 g, 35.47 mmol) was added, followed by stirring for 30 minutes. Di-tert-butyl dicarbonate (1.2 eq., 3.10 g, 14.18 mmol) was added, and the mixture was stirred at room temperature overnight. THF was removed by reducing the pressure of the reaction solution, and then the pH was adjusted to about 2.5 with 1N HCl aqueous solution. Ethyl acetate (EA) was added, and the resulting mixture was extracted twice. Then, the organic layer was dried, filtered, and concentrated with anhydrous magnesium sulfate to obtain 2-((tert-butoxycarbonyl)amino)-2-(2-fluorophenyl)acetic acid as a pale yellow solid (3.0 g, 94%).

Step (2) Synthesis of methyl 4-((tert-butoxycarbonyl)amino)-4-(2-fluorophenyl)-3-oxobutanoate 2-((tert-Butoxycarbonyl)amino)-2-(2-fluorophenyl)acetic acid (1.0 eq., 30.0 g, 111.4 mmol) and carbonyldiimidazole (1.03 eq., 18.6 g, 114.7 mmol) were dissolved in acetonitrile (300 mL) and stirred at room temperature for 1 hour. To another flask, monomethyl potassium malonate (1.03 eq., 17.9 g, 114.7 mmol), anhydrous magnesium chloride (1.03 eq., 10.94 g, 114.7 mmol), acetonitrile (300 mL), and triethylamine (1.03 eq., 16 mL, 114.7 mmol) were added and stirred at room temperature for 1 hour. The reactants of the two flasks prepared earlier were mixed using a cannula, and refluxed at 80° C. for 1 hour. After completion of the reaction, the mixture was cooled to room temperature, and water was added thereto. The mixture was cooled with ice, and stirred for 1 hour. The obtained solid was filtered, EA and water were added, and then the pH was adjusted to about 5 using 1N HCl. The mixture was extracted twice with EA, dried, filtered, and concentrated with anhydrous magnesium sulfate to obtain methyl 4-((tert-butoxycarbonyl)amino)-4-(2-fluorophenyl)-3-oxobutanoate as a solid (19.0 g, 52%).

Step (3) Synthesis of 1-(tert-butyl) 3-methyl 5-(fluorophenyl)-4-hydroxy-1H-pyrrole-1,3-dicarboxylate Methyl 4-((tert-butoxycarbonyl)amino)-4-(2-fluorophenyl)-3-oxobutanoate (1.0 eq., 15.4 g, 47.33 mmol) and N,N-dimethylformamide dimethyl acetal (3.0 eq., 19 mL, 142.00 mmol) were added to toluene (300 mL) and stirred at 40° C. for 4 hours to complete the reaction. The mixture was evaporated under reduced pressure to remove toluene, and EA and water were added. After neutralization to about pH 7 using 1N HCl, the mixture was extracted twice with EA. The organic layer was dried, filtered, and concentrated with anhydrous magnesium sulfate to obtain 1-(cert-butyl) 3-methyl 5-(fluorophenyl)-4-hydroxy-1H-pyrrole-1,3-dicarboxylate as a solid (14.28 g, 90%).

Step (4) Synthesis of 1-(tert-butyl) 3-methyl 5-(2-fluorophenyl)-4-methoxy-1H-pyrrole-1,3-dicarboxylate 1-(tert-Butyl) 3-methyl 5-(fluorophenyl)-4-hydroxy-1H-pyrrole-1,3-dicarboxylate (1.0 eq., 14.28 g, 42.58 mmol), potassium carbonate (2.0 eq., 11.8 g, 85.17 mmol), and dimethyl sulfate (1.13 eq., 4.56 mL, 48.12 mmol) were dissolved in acetone (213 mL) and stirred at 50° C. overnight. The reaction was completed by adding water, and then the excess acetone was removed by evaporation under reduced pressure. After adding EA and water, the mixture was neutralized to about pH 7 using 1N HCl, and then extracted twice with EA. The organic layer was dried, filtered, and concentrated with anhydrous magnesium sulfate, and purified by silica column chromatography to obtain 1-(cert-butyl) 3-methyl 5-(2-fluorophenyl)-4-methoxy-1H-pyrrole-1,3-dicarboxylate as a solid (14.00 g, 94%).

Step (5) Synthesis of methyl 5-(2-fluorophenyl)-4-methoxy-1H-pyrrole-3-carboxylate (Intermediate 1)

1-(tert-Butyl) 3-methyl 5-(2-fluorophenyl)-4-methoxy-1H-pyrrole-1,3-dicarboxylate (1.0 eq., 7.0 g, 20.0 mmol) and trifluoroacetic acid (10.0 eq., 15.3 mL, 200.4 mmol) were dissolved in dichloromethane (35 mL) and stirred at room temperature for 6 hours. After cooling to 0 to 5° C. using ice water, water was added and the pH was adjusted to 7.0 using 50% NaOH aqueous solution. After twice extraction with EA and evaporation, n-hexane was added. Then, the mixture was stirred for 1 hour and filtered to obtain methyl 5-(2-fluorophenyl)-4-methoxy-1H-pyrrole-3-carboxylate obtained as a pale pink solid (4.6 g, 92%).

$^1$H NMR (400 MHz, DMSO-$d_6$) δ 11.46 (s, 1H), 7.64 (dt, J=1.6, 7.8 Hz, 1H), 7.36-7.24 (m, 4H), 3.73 (s, 6H).

[Intermediate 2] tert-Butyl ((5-(2-fluorophenyl) methoxy-1H-pyrrol-3-yl)methyl)(methyl)carbamate Step (1) Synthesis of tert-butyl 2-(2-fluorophenyl)-4-(hydroxymethyl)-3-methoxy-1H-pyrrole-1-carboxylate Diisobutylaluminum hydride (1M hexane solution, 5 eq., 64.4 mL, 64.4 mmol) was dissolved in tetrahydrofuran (200 mL), and 1-(cert-butyl) 3-methyl 5-(2-fluorophenyl)-4-methoxy-1H-pyrrole-1,3-dicarboxylate (4.5 g, 12.9 mmol) was slowly added dropwise at 0° C., and stirred at room temperature for 1 hour. Water and a 1N aqueous NaOH solution were sequentially added dropwise, dried over anhydrous magnesium sulfate, filtered through celite, and concentrated. The concentrated residue was purified by column chromatography to obtain Cert-butyl 2-(2-fluorophenyl)-4-(hydroxymethyl)-3-methoxy-1H-pyrrole-1-carboxylate as a colorless oil (1.7 g, 41.1%).

$^1$H NMR (400 MHz, CDCl$_3$): δ 7.41-7.33 (m, 2H), 7.30 (s, 1H), 7.19 (dt, J=7.4 Hz, J=1.2 Hz, 1H), 7.10 (dt, J=9.0 Hz, J=0.8 Hz, 1H), 4.61 (d, J=4.8 Hz, 2H), 3.60 (s, 3H), 1.32 (s, 9H)

Step (2) Synthesis of tert-butyl 2-(2-fluorophenyl)-4-formyl-3-methoxy-1H-pyrrole-1-carboxylate tert-Butyl 2-(2-fluorophenyl)-4-(hydroxymethyl) methoxy-1H-pyrrole-1-carboxylate (1.7 g, 5.3 mmol) was dissolved in dichloromethane (20 mL), and Dess-Martin periodinane (1 eq., 2.24 g, 5.3 mmol) was slowly added dropwise and stirred at room temperature for 1 hour. Celite was added to the reaction mixture. The resulting product was concentrated and purified by column chromatography to obtain (5-(2-fluorophenyl)-4-methoxy-1H-pyrrol-3-yl) methanol as a colorless oil (1.23 g, 72.8%).

$^1$H NMR (400 MHz, CDCl$_3$): δ 9.89 (s, 1H), 7.92 (s, 1H), 7.42-7.37 (m, 2H), 7.22 (dt, J=7.5 Hz, J=0.9 Hz, 1H), 7.12 (dt, J=9.2 Hz, J=0.9 Hz, 1H), 3.75 (s, 3H), 1.38 (s, 9H)

Step (3) Synthesis of 5-(2-fluorophenyl)-4-methoxy-1H-pyrrole-3-carbaldehyde tert-Butyl 2-(2-fluorophenyl)-4-formyl-3-methoxy-1H-pyrrole-1-carboxylate (1.2 g, 3.8 mmol) was dissolved in water/methanol (1/3, 20 mL), potassium carbonate (3 eq., 1.6 g, 11.3 mmol) was added dropwise, and then the mixture was stirred at 100° C. for 2.5 hours. The reaction product was dried over anhydrous sodium sulfate and filtered to obtain 5-(2-fluorophenyl)-4-methoxy-1H-pyrrole-3-carbaldehyde as a yellow solid (800.0 mg, 97.1%).

$^1$H NMR (400 MHz, CDCl$_3$): δ 9.87 (s, 1H), 9.11 (brs, 1H), 8.17-8.13 (m, 1H), 7.34 (d, J=4.0 Hz, 1H), 7.27-7.23 (m, 2H), 7.19-7.16 (m, 1H), 3.98 (s, 3H)

Step (4) Synthesis of tert-butyl ((5-(2-fluorophenyl)-4-methoxy-114-pyrrol-3-yl)methyl)(methyl) carbamate (Intermediate 2)
5-(2-Fluorophenyl)-4-methoxy-1H-pyrrole carbaldehyde (800 mg, 3.65 mmol) was dissolved in methanol (50 mL), 40% methylamine solution (2.3 eq., 0.86 mL, 8.4 mmol) was added dropwise, and the mixture was stirred at room temperature for 30 minutes. The reaction mixture was cooled to 0° C., sodium borohydride (1.5 eq., 207.1 mg, 5.5 mmol) was added dropwise, and then the mixture was stirred at room temperature for 30 minutes. Water (150 mL) was added dropwise to the reaction mixture, the resulting product was stirred for 1 hour at the same temperature, and brine was added dropwise, followed by extraction with EA. The extracted organic layer was dried, filtered, and concentrated with anhydrous magnesium sulfate. The concentrated residue was dissolved in acetonitrile (40 mL), and then di-tert-butyl dicarbonate (1.2 eq., 955.7 mg, 4.4 mmol) was added dropwise, followed by stirring at room temperature for 2 hours. Water and EA were added dropwise to the reaction mixture for extraction, and the organic layer was dried, filtered, and concentrated with anhydrous magnesium sulfate. The concentrated residue was purified by column chromatography to obtain Cert-butyl ((5-(2-fluorophenyl)-4-methoxy-1H-pyrrol yl)methyl) (methyl)carbamate as a light brown solid (946.8 mg, 78.9%).

$^1$H NMR (400 MHz, CDCl$_3$): δ 8.55 (brs, 1H), 8.07 (dt, J=7.9 Hz, J=1.7 Hz, 1H), 7.20-7.06 (m, 1H), 6.62 (s, 1H), 4.35 (s, 2H), 3.72 (s, 3H), 2.86 (s, 3H), 1.50 (s, 9H)

[Intermediate 3] Methyl 5-(2,4-difluorophenyl)-4-methoxy-1H-pyrrole-3-carboxylate

Step (1) Synthesis of 2-((tert-butoxycarbonyl)amino)-2-(2,4-difluorophenyl)acetic acid 2-Amino-2-(2,4-difluorophenyl)acetic acid (1.0 eq., 7.22 g, 38.6 mmol) was dissolved in THF/H$_2$O (1:1, 200 mL), and then cooled to 0° C. NaHCO$_3$ (3.0 eq., 9.74 g, 116 mmol) and Boc$_2$O (1.2 eq., 10.64 mL, 46.3 mmol) were added, and after stirring at room temperature overnight, water was added to the reaction solution, and the pH was adjusted to 2.5. Then, the resulting mixture was extracted with EA. The organic layer was dried, filtered, and concentrated with anhydrous magnesium sulfate to obtain 2-((tert-butoxycarbonyl)amino)-2-(2,4-difluorophenyl)acetic acid (17.35 g, 99%) as a white solid without further purification. [M+Na]+: 310

Step (2) Synthesis of methyl 4-((tert-butoxycarbonyl)amino)-4-(2,4-difluorophenyl)-3-oxobutanoate 2-((tert-Butoxycarbonyl)amino)-2-(2,4-difluorophenyl) acetic acid (1.0 eq., 38.6 mmol) and carbonyldiimidazole (1.1 eq., 6.89 g, 42.5 mmol) were dissolved in acetonitrile (100 mL). In another flask, methyl potassium malonate (1.1 eq., 6.64 g, 42.5 mmol), triethylamine (1.1 eq., 5.97 mL, 42.5 mmol), magnesium chloride (1.1 eq., 4.05 g, 42.5 mmol) were dissolved in acetonitrile. (100 mL). After each solution was stirred at room temperature for 1 hour, the two solutions prepared above were combined and stirred at 80° C. for 3 hours. After adding H$_2$O (100 mL), the mixture was stirred at room temperature for 2 hours, and the resulting solid was filtered. EA and water were added to the filtered solid, and the mixture was stirred at room temperature for 10 minutes and neutralized to pH 7 with aq. HCl. The organic layer extracted with EA was dried, filtered, and concentrated with anhydrous magnesium sulfate, concentrated to obtain methyl 4-((tert-butoxycarbonyl)amino)-4-(2,4-difluorophenyl)-3-oxobutanoate (12.64 g, 95%) as a brown liquid without further purification.

$^1$H NMR (400 MHz, CDCl$_3$): δ 7.33-7.28 (m, 1H), 6.97-6.87 (m, 2H), 5.85 (brs, 1H), 5.67 (d, J=6.8 Hz, 1H), 3.70 (s, 3H), 3.53 (d, J=16.0 Hz, 1H), 4.75 (d, J=16.0 Hz, 1H), 1.34 (s, 9H).

Step (3) Synthesis of 1-(tert-butyl) 3-methyl 5-(2,4-difluorophenyl)-4-hydroxy-1H-pyrrole-1,3-dicarboxylate Methyl 4-((tert-butoxycarbonyl)amino)-4-(2,4-difluorophenyl)-3-oxobutanoate (1.0 eq., 12.64 g, 36.8 mmol) and N,N-dimethylformamide dimethyl acetal (3 eq., 14.7 mL, 110.4 mmol) were dissolved in toluene (184 mL) and stirred at 40° C. for 5 hours. After concentration, EA and water were added, and the mixture was neutralized to pH 7 with 1N HCl. The organic layer extracted with EA was dried, filtered, and concentrated with anhydrous magnesium sulfate to obtain 1-(cert-butyl) 3-methyl 5-(2,4-difluorophenyl)-4-hydroxy-1H-pyrrole-1,3-dicarboxylate as a brown liquid without further purification.

$^1$H NMR (400 MHz, CDCl$_3$): δ 7.75 (s, 1H), 7.52 (s, 1H), 7.43 (dt, J=8.4, 6.8 Hz, 1H), 6.98-6.84 (m, 2H), 3.92 (s, 3H), 1.41 (s, 9H).

Step (4) Synthesis of 1-(tert-butyl) 3-methyl 5-(2,4-difluorophenyl)-4-methoxy-1H-pyrrole-1,3-dicarboxylate 1-(tert-Butyl) 3-methyl 5-(2,4-difluorophenyl)-4-hydroxy-1H-pyrrole-1,3-dicarboxylate (1.0 eq., 36.8 mmol), potassium carbonate (2.0 eq., 10.2 g, 73.6 mmol), and dimethyl sulfate (1.2 eq., 4.2 mL, 44.2 mmol) were dissolved in acetone (184 mL), and stirred at 40° C. overnight. EA and water were added, and the mixture was neutralized to pH 7 with 1N HCl. The organic layer extracted with EA was dried, filtered, and concentrated with anhydrous magnesium sulfate, purified by silica chromatography to obtain 1-(cert-butyl) 3-methyl 5-(2,4-difluorophenyl)-4-methoxy-1H-pyrrole-1,3-dicarboxylate (12.86 g, 95%) as a yellow liquid. [M+H]+: 367

$^1$H NMR (400 MHz, CDCl$_3$): δ 7.90 (s, 1H), 7.36 (dt, J=8.4, 6.4 Hz, 1H), 6.99-6.86 (m, 2H), 3.90 (s, 3H), 3.70 (s, 3H), 1.41 (s, 9H).

Step (5) Synthesis of methyl 5-(2,4-difluorophenyl) methoxy-1H-pyrrole-3-carboxylate (Intermediate 3)

1-(tert-Butyl) 3-methyl 5-(2,4-fluorophenyl)-4-methoxy-1H-pyrrole-1,3-dicarboxylate (1.0 eq., 12.8 g, 34.8 mmol) and trifluoroacetic acid (10 eq., 26 mL, 348 mmol) were dissolved in dichloromethane (70 mL) and stirred at room temperature for 5 hours. Water (100 mL) was added at 0° C. and the mixture was neutralized to pH 7 with 1N NaOH. The reaction solution was extracted with EA. The organic layer was dried, filtered, and concentrated with anhydrous magnesium sulfate, and solidified with hexane and EA to obtain methyl 5-(2,4-difluorophenyl)-4-methoxy-1H-pyrrole-3-carboxylate as a pale pink solid (4.98 g, 54%) without further purification.

$^1$H NMR (400 MHz, CDCl$_3$): δ 8.82 (brs, 1H), 8.14 (dt, J=9.1, 6.5 Hz, 1H), 7.33 (d, J=3.6 Hz, 1H), 7.01-6.87 (m, 2H), 3.89 (s, 3H), 3.88 (s, 3H).

[Intermediate 4] tert-Butyl ((5-(2,4-difluorophenyl)-4-methoxy-1H-pyrrol-3-yl)methyl)(methyl)carbamate

Step (1) Synthesis of tert-butyl 2-(2,4-difluorophenyl)-4-(hydroxymethyl)-3-methoxy-1H-pyrrole-1-carboxylate 1-(tert-Butyl) 3-methyl 5-(2,4-difluorophenyl) methoxy-1H-pyrrole-1,3-dicarboxylate (1.0 eq., 10.02 g, 27.3 mmol) was dissolved in THF (137 mL) and cooled to 0° C. 1.0 M DIBAL-H (8.0 eq., 219 mL, 219 mmol) was slowly added in THF. The reaction solution was stirred at room temperature for 2 hours. After cooling to 0° C., H$_2$O (8.76 mL), 15% NaOH (8.76 mL), and H$_2$O (22 mL) were sequentially added. Then, after stirring at room temperature for 20 minutes, anhydrous magnesium sulfate was added, and the mixture was stirred for 20 minutes and filtered through Celite. After concentration, purification was performed by silica chromatography to obtain Cert-butyl 2-(2,4-difluorophenyl)-4-(hydroxymethyl)-3-methoxy-1H-pyrrole-1-carboxylate (5.13 g, 55%).

¹H NMR (400 MHz, CDCl₃): δ 7.35 (dt, J=8.4, 6.4 Hz, 1H), 7.29 (s, 1H), 6.97-6.85 (m, 2H), 4.6 (s, 2H), 3.60 (s, 3H), 1.37 (s, 9H).

Step (2) Synthesis of tert-butyl 2-(2,4-difluorophenyl)-4-formyl-3-methoxy-1H-pyrrole-1-carboxylate tert-Butyl 2-(2,4-difluorophenyl)-4-(hydroxymethyl)-3-methoxy-1H-pyrrole-1-carboxylate (1.0 eq., 5.13 g, 15.1 mmol) was dissolved in dichloromethane (76 mL) and cooled to 0° C. DMP (1.1 eq., 7.04 g, 16.6 mmol) was added, followed by stirring at room temperature for 30 minutes. The reaction solution was washed with aq. NaOH and then extracted with EA. The organic layer was dried, filtered, and concentrated with anhydrous magnesium sulfate, and purified by silica chromatography to obtain Cert-butyl 2-(2,4-difluorophenyl)-4-formyl-3-methoxy-1H-pyrrole-1-carboxylate (3.56 g, 70%) as a yellow solid.

¹H NMR (400 MHz, CDCl₃): δ 9.88 (s, 1H), 7.91 (s, 1H), 7.36 (dt, J=8.4, 6.4 Hz, 1H), 7.00-6.90 (m, 2H), 3.75 (s, 3H), 1.41 (s, 9H).

Step (3) Synthesis of 5-(2,4-difluorophenyl)-4-methoxy-1H-pyrrole-3-carbaldehyde tert-Butyl 2-(2,4-difluorophenyl)-4-formyl-3-methoxy-1H-pyrrole-1-carboxylate (1.0 eq., 3.56 g, 10.6 mmol) and potassium carbonate (3 eq., 4.40 g, 31.8 mmol) were dissolved in methanol/H₂O (3:1, 104 mL), and stirred at 110° C. for 1 hour. After concentration, the concentrated product was filtered with acetone, and solidified with dichloromethane and hexane to obtain 5-(2,4-difluorophenyl)-4-methoxy-1H-pyrrole-3-carboaldehyde (2.17 g, 86%) as an orange solid without further purification.

¹H NMR (400 MHz, CDCl₃): δ 9.86 (s, 1H), 8.97 (brs, 1H), 8.12 (dt, J=9.0, 6.4 Hz, 1H), 7.33 (d, J=4.0 Hz, 1H), 7.03-6.91 (m, 2H), 3.96 (s, 3H).

Step (4) Synthesis of tert-butyl ((5-(2,4-difluorophenyl)-4-methoxy-1H-pyrrol-3-yl)methyl)(methyl)carbamate (Intermediate 4)

2.0 M methyl amine was dissolved in methanol (90 mL), followed by stirring at room temperature for 30 minutes in 5-(2,4-Difluorophenyl)-4-methoxy-1H-pyrrole-3-carboaldehyde (1.0 eq., 2.17 g, 9.15 mmol), THF (10 eq., 46 mL, 91.5 mmol). NaBH₄ (5 eq., 1.73 g, 45.8 mmol) was added and the mixture was stirred at room temperature for 30 minutes. Then, water was added and the mixture was stirred for an additional 30 minutes. The reaction solution was washed with brine and extracted with EA. The organic layer was dried, filtered, and concentrated with anhydrous magnesium sulfate. Then, the concentrated product was dissolved immediately in acetonitrile (46 mL), Boc₂O (1.2 eq., 2.53 mL, 11.0 mmol) was slowly added thereto, and the resulting mixture was stirred at room temperature for 1 hour. Water was added to the reaction solution, followed by extraction with EA. The organic layer was dried, filtered, and concentrated with anhydrous magnesium sulfate, and purified by silica chromatography to obtain Cert-butyl 5-(2, 4-difluorophenyl)-4-methoxy-1H-pyrrol-3-yl)methyl)(methyl)carbamate (2.46 g, 76%) as a brown solid.

¹H NMR (400 MHz, CDCl₃): δ 8.45 (brs, 1H), 8.05 (dt, J=9.0, 6.5 Hz, 1H), 6.98-6.85 (m, 2H), 6.63 (brs, 1H), 4.37 (brs, 2H), 3.73 (s, 3H), 2.88 (s, 3H), 1.52 (s, 9H).

Compounds of Examples 1 to 6 below were synthesized using the synthesized intermediates 1 to 4. The synthesis methods thereof are based on Reaction Schemes 1 and 2 above. As an example of the preparation for the Example compounds above, the preparation methods of Examples 1 to 6 below were specifically described.

Hereinafter, the synthesis methods of Examples 1 to 6 are shown in detail.

Synthesis Example 1. Synthesis of Example 1

[Example 1] 1-(5-(2-Fluorophenyl)-4-methoxy-1-((6-methoxypyridin-3-yl)sulfonyl)-1H-pyrrol-3-yl)-N-methylmethanamine Step (1) Synthesis of methyl 5-(2-fluorophenyl)-4-methoxy-1-((6-methoxypyridin-3-yl)sulfonyl)-1H-pyrrole-3-carboxylate Methyl 5-(2-fluorophenyl)-4-methoxy-1H-pyrrole-3-carboxylate (intermediate 1, 1.0 eq., 1.2 g, 4.8 mmol) was dissolved in THF (20.0 mL), and NaH (2.0 eq., 384.8 mg, 9.6 mmol) was added dropwise at 0° C., followed by stirring at room temperature for 10 minutes. 6-Methoxypyridine-3-sulfonyl chloride (1.5 eq., 1.6 g, 7.2 mmol) was added, followed by stirring at room temperature for 1 hour. Water was added to the reaction solution, and the resulting solution was extracted with EA. The organic layer was dried, filtered, and concentrated with anhydrous magnesium sulfate, and purified by column chromatography to obtain methyl 5-(2-fluorophenyl)-4-methoxy-1-((6-methoxypyridin-3-yl)sulfonyl)-1H-pyrrole-3-carboxylate as a light brown solid (1.85 g, 91.6%).

Step (2) Synthesis of 5-(2-fluorophenyl)-4-methoxy ((6-methoxypyridin-3-yl)sulfonyl)-1H-pyrrol-3-yl) methanol Methyl 5-(2-fluorophenyl)-4-methoxy-1-((6-methoxypyridin-3-yl)sulfonyl)-1H-pyrrole-3-carboxylate (1.0 eq., 1.0 g, 2.38 mmol) was dissolved in THF (5.0 mL), and DIBAL 1.0 M was added dropwise in n-hexane solution (5.0 eq., 11.9 mL, 11.9 mmol) at 0° C., followed by stirring at room temperature for 1 hour. The reaction solution was cooled to 0° C., the reaction was completed with an aqueous Rochelle salt solution, and the resulting solution was extracted with EA. The organic layer was dried, filtered, and concentrated with anhydrous magnesium sulfate, and purified by column chromatography to obtain 5-(2-fluorophenyl)-4-methoxy-1-((6-methoxypyridin-3-yl)sulfonyl)-1H-pyrrol-3-yl)methanol as a yellow oil (654.8 mg, 70.2%).

Step (3) Synthesis of methyl 5-(2-fluorophenyl)-4-methoxy-1-((6-methoxypyridin-3-yl)sulfonyl)-114-pyrrole-3-carbaldehyde 5-(2-Fluorophenyl)-4-methoxy-1-((6-methoxypyridin-3-yl)sulfonyl)-1H-pyrrol-3-yl)methanol (1.0 eq., 500.0 mg, 1.3 mmol) and Dess-Martin periodinane (1.0 eq., 540.4 mg, 1.3 mmol) were dissolved in DCM (10.0 mL) and stirred at room temperature for 1 hour. The reaction product was concentrated and purified by column chromatography to obtain 5-(2-fluorophenyl)-4-methoxy-1-((6-methoxypyridin yl)sulfonyl)-1H-pyrrole-3-carbaldehyde as a pale dark blue solid (388.2 mg, 78.1%).

Step (4) Synthesis of 1-(5-(2-Fluorophenyl)-4-methoxy-1-((6-methoxypyridin-3-yl)sulfonyl)-1H-pyrrol-3-yl)-N-methylmethanamine 5-(2-Fluorophenyl)-4-methoxy-1-((6-methoxypyridin-3-yl)sulfonyl)-1H-pyrrole-3-carbaldehyde (1.0 eq., 385.0 mg, 0.99 mmol) was dissolved in THF (5.0 mL), and 2.0 M of methylamine was added in THF (10 eq., 4.9 mL, 9.9 mmol). After stirring at room temperature for 1 hour, the reaction product was cooled to 0° C., NaBH$_4$ (10 eq., 373.4 mg, 9.9 mmol) was added, and the resulting mixture was stirred at room temperature for 1 hour. To the reaction solution, 6.0N aqueous hydrogen chloride solution was slowly added dropwise, and the resulting solid was filtered. The filtered solid was dissolved in water, and 1N aqueous sodium hydroxide solution was added thereto, followed by extraction with EA.

The organic layer was dried, filtered, and concentrated with anhydrous magnesium sulfate to obtain 1-(5-(2-fluorophenyl)-4-methoxy-1-((6-methoxypyridin-3-yl)sulfonyl)-1H-pyrrol-3-yl)-N-methylmethanamine as a white solid (125.8 mg, 28.3%) [M+H]+: 405.

Synthesis Example 2. Synthesis of Example 2

[Example 2] 1-(5-(2,4-Difluorophenyl)-4-methoxy ((6-methoxypyridin-3-yl)sulfonyl)-1H-pyrrol-3-yl)-N-methylmethanamine Step (1) Synthesis of methyl 5-(2,4-difluorophenyl) methoxy-1-((6-methoxypyridin-3-yl)sulfonyl)-1H-pyrrole carboxylate Methyl 5-(2,4-difluorophenyl)-4-methoxy-1H-pyrrole-3-carboxylate (intermediate 3, 1.0 eq., 802 mg, 3.00 mmol) and NaH (1.5 eq., 180 mg, 4.5 mmol) were dissolved in anhydrous DMF (15.0 mL) and stirred at room temperature for 10 minutes. 6-Methoxypyridine-3-sulfonyl chloride (1.5 eq., 934 mg, 4.50 mmol) was added, followed by stirring at room temperature for 1 hour. After adding distilled water to the reaction solution, the resulting solution was washed with brine and extracted with EA. The organic layer was dried, filtered, and concentrated with anhydrous magnesium sulfate, and purified by column chromatography to obtain methyl 5-(2,4-difluorophenyl)-4-methoxy-1-((6-methoxypyridin-3-yl)sulfonyl)-1H-pyrrole-3-carboxylate (1.09 g, 83%).

Step (2) Synthesis of (5-(2,4-difluorophenyl)-4-methoxy-1-((6-methoxypyridin-3-yl)sulfonyl)-1H-pyrrol-3-yl)methanol Methyl 5-(2,4-difluorophenyl)-4-methoxy-1-((6-methoxypyridin-3-yl)sulfonyl)-1H-pyrrole-3-carboxylate (1.0 eq., 1.09 g, 2.49 mmol) was dissolved in anhydrous THF (13.0 mL), and then DIBAL 1.0 M was added dropwise in THF (5.0 eq., 12.4 mL, 12.4 mmol) at 0° C. Then, the reaction solution was stirred at room temperature for 4 hours. To the reaction solution, 0.50 mL of water, 0.5 mL of 1N aqueous sodium hydroxide solution, and 1.25 mL of water were sequentially added. Then, the resulting mixture was stirred for 30 minutes, and anhydrous magnesium sulfate was added, followed by stirring for 30 minutes. The resulting product was dried, filtered, concentrated, and purified by column chromatography to obtain (5-(2,4-difluorophenyl)-4-methoxy-1-((6-methoxypyridin-3-yl)sulfonyl)-1H-pyrrol-3-yl)methanol (869 mg, 85%).

Step (3) Synthesis of 5-(2,4-difluorophenyl)-4-methoxy-1-((6-methoxypyridin-3-yl)sulfonyl)-1H-pyrrole-3-carbaldehyde 5-(2,4-Difluorophenyl)-4-methoxy-1-((6-methoxypyridin-3-yl) sulfonyl)-1H-pyrrol-3-yl)methanol (1.0 eq., 869 mg, 2.12 mmol) and Dess-Martin periodinane (1.1 eq., 988 mg, 2.33 mmol) were dissolved in DCM (21.0 mL) and stirred at room temperature for 30 minutes. NaHCO$_3$ aqueous solution was added to the reaction solution, and the resulting solution was washed with Na$_2$S$_2$O$_3$ aqueous solution and extracted with EA. The organic layer was dried, filtered, and concentrated with anhydrous magnesium sulfate, and purified by column chromatography to obtain 5-(2,4-difluorophenyl)-4-methoxy-1-((6-methoxypyridin yl)sulfonyl)-1H-pyrrole-3-carbaldehyde (824 mg, 95%).

Step (4) Synthesis of 1-(5-(2,4-difluorophenyl) methoxy-1-((6-methoxypyridin-3-yl)sulfonyl)-1H-pyrrol yl)-N-methylmethanamine 5-(2,4-Difluorophenyl)-4-methoxy-1-((6-methoxypyridin-3-yl)sulfonyl)-1H-pyrrole-3-carbaldehyde (1.0 eq., 824 mg, 2.02 mmol) was dissolved in THF (20.0 mL), and 2.0M of methylamine was added in THF (20 eq., 20.2 mL, 40.4 mmol). After stirring at room temperature for 3 hours, NaBH$_4$ (10 eq., 764 mg, 20.2 mmol) was added, followed by stirring for 18 hours. After adding distilled water to the reaction solution, the resulting solution was washed with brine and extracted with EA. The organic layer was dried, filtered, and concentrated with anhydrous magnesium sulfate, and purified by column chromatography to obtain 1-(5-(2,4-difluorophenyl)-4-methoxy-1-((6-methoxypyridin-3-yl)sulfonyl)-1H-pyrrol-3-yl)-N-methylmethanamine as a red syrup (90.0 mg, 10%) [M+H]$^+$: 423.

Synthesis Example 3. Synthesis of Example 3

[Example 3] 1-(5-(2,4-Difluorophenyl)-4-methoxy-1-((6-methylpyridin-3-yl)sulfonyl)-1H-pyrrol-3-yl)-N-methylmethanamine Step (1) Synthesis of methyl 5-(2,4-difluorophenyl)-4-methoxy-1-((6-methylpyridin-3-yl)sulfonyl)-1H-pyrrole-3-carboxylate Methyl 5-(2,4-difluorophenyl)-4-methoxy-1H-pyrrole carboxylate (intermediate 3, 1.0 eq., 534 mg, 2.0 mmol) and NaH (1.5 eq., 120 mg, 3.0 mmol) were dissolved in anhydrous DMF (10.0 mL) and stirred at 50° C. for 50 minutes. 6-Methylpyridine-3-sulfonyl chloride (1.5 eq., 575 mg, 3.0 mmol) was added, followed by stirring at 50° C. for 16 hours. After adding distilled water to the reaction solution, the resulting solution was washed with brine and extracted with EA. The organic layer was dried, filtered, and concentrated with anhydrous magnesium sulfate, and purified by column chromatography to obtain methyl 5-(2,4-difluorophenyl)-4-methoxy-1-((6-methylpyridin-3-yl)sulfonyl)-1H-pyrrole-3-carboxylate (614 mg, 73%).

Step (2) Synthesis of (5-(2,4-difluorophenyl)-4-methoxy-1-((6-methylpyridin-3-yl)sulfonyl)-1H-pyrrol-3-yl)methanol Methyl 5-(2,4-difluorophenyl)-4-methoxy-1-((6-methylpyridin-3-yl)sulfonyl)-1H-pyrrole-3-carboxylate (1.0 eq., 614 mg, 1.45 mmol) was dissolved in anhydrous THF (7.27 mL), and then DIBAL 1.0M was added dropwise in THF (5.0 eq., 7.27 mL, 7.27 mmol) at 0° C. Then, the resulting mixture was stirred at room temperature for 30 minutes. To the reaction solution, 0.29 mL of water, 0.29 mL of 15% aqueous sodium hydroxide solution, and 0.73 mL of water were sequentially added. Then, the resulting mixture was stirred for 14 hours. Anhydrous magnesium sulfate was added, followed by stirring for 30 minutes. The resulting product was dried, filtered, concentrated, and purified by column chromatography to obtain (5-(2,4-difluorophenyl)-4-methoxy-1-((6-methylpyridin-3-yl)sulfonyl)-1H-pyrrol-3-yl)methanol as a yellow solid (494 mg, 86%).

Step (3) Synthesis of 5-(2,4-difluorophenyl)-4-methoxy-1-((6-methylpyridin-3-yl)sulfonyl)-1H-pyrrole-3-carbaldehyde 5-(2,4-Difluorophenyl)-4-methoxy-1-((6-methylpyridin-3-yl)sulfonyl)-1H-pyrrol-3-yl)methanol (1.0 eq., 494 mg, 1.25 mmol) and Dess-Martin periodinane (1.1 eq., 583 mg, 1.38 mmol) were dissolved in DCM (12.0 mL) and stirred at room temperature for 40 minutes. An aqueous sodium hydroxide solution was added to the reaction solution, followed by extraction with EA. The organic layer was dried, filtered, and concentrated with anhydrous magnesium sulfate, and purified by column chromatography to obtain 5-(2,4-difluorophenyl)-4-methoxy-1-((6-methylpyridin-3-yl)sulfonyl)-1H-pyrrole-3-carbaldehyde (422 mg, 86%).

Step (4) Synthesis of 1-(5-(2,4-difluorophenyl)-4-methoxy-1-((6-methylpyridin-3-yl)sulfonyl)-1H-pyrrol-3-yl)-N-methylmethanamine 5-(2,4-Difluorophenyl)-4-methoxy-1-((6-methylpyridin-3-yl)sulfonyl)-1H-pyrrole-3-carbaldehyde (1.0 eq., 422 mg, 1.07 mmol) was dissolved in MeOH (5.0 mL), and 2.0M of methylamine was added in THF (10 eq., 5.2 mL, 10.7 mmol). After stirring at room temperature for 30 minutes, NaBH$_4$ (5 eq., 204 mg, 5.38 mmol) was added, followed by stirring for 10 minutes. After adding NaHCO$_3$ aqueous solution to the reaction solution, the resulting solution was washed with brine and extracted with EA. The organic layer was dried, filtered, and concentrated with anhydrous magnesium sulfate, and purified by column chromatography to obtain 1-(5-(2,4-difluorophenyl)-4-methoxy-1-((6-methylpyridin-3-yl)sulfonyl)-1H-pyrrol-3-yl)-N-methylmethanamine as a yellow solid (176 mg, 40%) [M+H]+: 408.

Synthesis Example 4. Synthesis of Example 4

[Example 4] 1-(5-(2-Fluorophenyl)-4-methoxy-1-((6-methylpyridin-3-yl)sulfonyl)-1H-pyrrol-3-yl)-N-methylmethanamine

Step (1) Synthesis of tert-butyl ((5-(2-fluorophenyl)-4-methoxy-1-((6-methylpyridin-3-yl)sulfonyl)-1H-pyrrol-3-yl)methyl)(methyl)carbamate tert-Butyl ((5-(2-fluorophenyl)-4-methoxy-1H-pyrrol-3-yl)methyl) (methyl)carbamate (intermediate 2, 100.0 mg, 0.3 mmol), NaH (24.0 mg, 0.6 mmol), and 15-crown-5-ether (0.9 mL, 0.5 mmol) were dissolved in anhydrous THF (1.5 mL) and stirred at 50° C. for 10 minutes. 6-Methylpyridine-3-sulfonyl chloride (86.0 mg, 0.5 mmol) was added and stirred at room temperature for 30 minutes. After adding distilled water to the reaction solution, the resulting solution was washed with brine and extracted with EA. The organic layer was dried, filtered, and concentrated with anhydrous magnesium sulfate, and purified by column chromatography to obtain Cert-butyl ((5-(2-fluorophenyl)-4-methoxy-1-((6-methylpyridin-3-yl)sulfonyl)-1H-pyrrol-3-yl)methyl) (methyl)carbamate as a pale yellow oil (60.9 mg, 42%).

Step (2) Synthesis of 1-(5-(2-fluorophenyl)-4-methoxy-1-((6-methylpyridin-3-yl)sulfonyl)-1H-pyrrol-3-yl)-N-methylmethanamine tert-Butyl ((5-(2-fluorophenyl)-4-methoxy-1-((6-methylpyridin-3-yl)sulfonyl)-1H-pyrrol-3-yl)methyl) (methyl)carbamate (60.0 mg, 0.1 mmol), and 1.0 M hydrogen chloride in an ethyl acetate solution (2.0 mL) were dissolved in ethanol (1.0 mL) and stirred at room temperature for 4 hours. After adding NaHCO$_3$ aqueous solution to the reaction solution, the resulting solution was washed with brine and extracted with EA. The organic layer was dried, filtered, and concentrated with anhydrous magnesium sulfate, and purified by column chromatography to obtain 1-(5-(2-fluorophenyl)-4-methoxy-1-((6-methylpyridin-3-yl)sulfonyl)-1H-pyrrole-3-yl)-N-methylmethanamine as a light yellow solid (49.8 mg, 62%) [M+H]+: 390.

Synthesis Example 5. Example 5

[Example 5] 1-5-(2,4-Difluorophenyl)-4-methoxy-1-((6-methylpyridin-2-yl)sulfonyl)-1H-pyrrol-3-yl)-N-methylmethanamine

Step (1) Synthesis of methyl 5-(2,4-difluorophenyl) methoxy-1-((6-methylpyridin-2-yl)sulfonyl)-1H-pyrrole-3-carboxylate Methyl 5-(2,4-difluorophenyl)-4-methoxy-1H-pyrrole-3-carboxylate (intermediate 3, 1.0 eq., 400.0 mg, 1.5 mmol) and NaH (1.5 eq., 90.0 mg, 2.25 mmol) were dissolved in anhydrous DMF (10.0 mL) and stirred at room temperature for 30 minutes. 6-Methylpyridine-2-sulfonyl chloride (1.5 eq., 430 mg, 2.25 mmol) was added, followed by stirring at room temperature for 5 hours. After adding distilled water to the reaction solution, the resulting solution was washed with brine and extracted with EA. The organic layer was dried, filtered, and concentrated with anhydrous magnesium sulfate, and purified by column chromatography to obtain methyl 5-(2,4-difluorophenyl)-4-methoxy-1-((6-methylpyridin-2-yl)sulfonyl)-1H-pyrrole-3-carboxylate as a clear syrup (442.0 mg, 70%).

Step (2) Synthesis of (5-(2,4-difluorophenyl)-4-methoxy-1-((6-methylpyridin-2-yl)sulfonyl)-1H-pyrrol-3-yl)methanol Methyl 5-(2,4-difluorophenyl)-4-methoxy-1-((6-methylpyridin-2-yl)sulfonyl)-1H-pyrrole-3-carboxylate (1.0 eq., 439.0 mg, 1.04 mmol) was dissolved in anhydrous THF (5.0 mL), and then DIBAL 1.0M was added dropwise in THF (3.0 eq., 3.12 mL, 3.12 mmol) at 0° C. Then, the reaction solution was stirred at room temperature for 2 hours. MeOH was added to the reaction solution, and then the resulting solution was washed with an aqueous Rochelle salt solution and extracted with EA. The organic layer was dried, filtered, and concentrated with anhydrous magnesium sulfate to obtain (5-(2,4-difluorophenyl)-4-methoxy-1-((6-methylpyridin-2-yl)sulfonyl)-1H-pyrrol-3-yl)methanol as yellow syrup (417.0 mg, 102%).

Step (3) Synthesis of 5-(2,4-difluorophenyl)-4-methoxy-1-((6-methylpyridin-2-yl)sulfonyl)-1H-pyrrole-3-carbaldehyde 5-(2,4-Difluorophenyl)-4-methoxy-1-((6-methylpyridin-2-yl)sulfonyl)-1H-pyrrol-3-yl)methanol (1.0 eq., 398.0 mg, 1.01 mmol) and Dess-Martin periodinane (1.0 eq., 428.0 mg, 1.01 mmol) were dissolved in DCM (10.0 mL) and stirred at room temperature for 5 hours. NaHCO$_3$ aqueous solution was added to the reaction solution, and the resulting solution was washed with Na$_2$S$_2$O$_3$ aqueous solution and extracted with EA. The organic layer was dried, filtered, and concentrated with anhydrous magnesium sulfate, and purified by column chromatography to obtain 5-(2,4-difluorophenyl)-4-methoxy-1-((6-methylpyridin-2-yl)sulfonyl)-1H-pyrrole carbaldehyde as a yellow syrup (331.0 mg, 84%).

Step (4) Synthesis of 1-5-(2,4-difluorophenyl) methoxy-1-((6-methylpyridin-2-yl)sulfonyl)-1H-pyrrol-3-yl)-N-methylmethanamine 5-(2,4-Difluorophenyl)-4-methoxy-1-((6-methylpyridin-2-yl)sulfonyl)-1H-pyrrole-3-carbaldehyde (1.0 eq., 331.0 mg, 0.84 mmol) was dissolved in MeOH (8.5 mL), and 9.8M of methylamine was added in MeOH (20 eq., 1.72 mL, 16.9 mmol). After stirring at room temperature for 1 hour, NaBH$_4$ (10 eq., 318.0 mg, 8.4 mmol) was added, followed by stirring for 30 minutes. After adding NaHCO$_3$ aqueous solution to the reaction solution, the resulting solution was washed with brine and extracted with EA. The organic layer was dried, filtered, and concentrated with anhydrous magnesium sulfate, and purified by column chromatography to obtain 1-5-(2,4-difluorophenyl)-4-methoxy-1-((6-methylpyridin-2-yl)sulfonyl)-1H-pyrrole-3-yl)-N-methylmethanamine as a yellow syrup (185.0 mg, 54%) [M+H]$^+$: 407.

Synthesis Example 6. Synthesis of Example 6

[Example 6] 1-(5-(2-Fluorophenyl)-4-methoxy-1-(pyridin-2-ylsulfonyl)-1H-pyrrol-3-yl)-N-methylmethanamine Step (1) Synthesis of tert-butyl ((5-(2-fluorophenyl)-4-methoxy-1-(pyridin-2-ylsulfonyl)-1H-pyrrol-3-yl)methyl)(methyl)carbamate tert-Butyl ((5-(2-fluorophenyl)-4-methoxy-1H-pyrrol-3-yl)methyl) (methyl)carbamate (intermediate 2, 1.0 eq.), NaH (1.5 eq., 90.0 mg, 2.25 mmol), and 15-crown-5-ether (catalytic amount) were dissolved in anhydrous THF (10.0 mL) and stirred at room temperature for 30 minutes. Pyridine-2-sulfonyl chloride (1.5 eq., 430 mg, 2.25 mmol) was added, followed by stirring at room temperature for 5 hours. After adding distilled water to the reaction solution, the resulting solution was washed with brine and extracted with EA. The organic layer was dried, filtered, and concentrated with anhydrous magnesium sulfate, and purified by column chromatography to obtain Cert-butyl ((5-(2-fluorophenyl)-4-methoxy-1-(pyridin-2-ylsulfonyl)-1H-pyrrol-3-yl)methyl) (methyl)carbamate as a brown oil (80 mg, 55%).

Step (2) Synthesis of 1-(5-(2-Fluorophenyl)-4-methoxy-1-(pyridin-2-ylsulfonyl)-1H-pyrrol-3-yl)-N-methylmethanamine tert-Butyl ((5-(2-fluorophenyl)-4-methoxy-1-(pyridin-2-ylsulfonyl)-1H-pyrrol-3-yl)methyl) (methyl)carbamate (0.17 eq., 80 mg) and trifluoroacetic acid (10.0 eq., 0.88 mL, 11.54 mmol) were dissolved in dichloromethane (2.3 mL) and stirred at room temperature for 6 hours. After removing the solvent by distillation under reduced pressure, the resulting product was cooled to 0 to 5° C. using ice water, then water was added and the pH was adjusted to 7.0 using an aqueous NaHCO$_3$ solution. After twice extraction with EA and evaporation, n-hexane was added, and the resulting product was stirred for 1 hour and filtered to obtain 1-(5-(2-fluorophenyl)-4-methoxy-1-(pyridin-2-ylsulfonyl)-1H-pyrrol-3-yl)-N-methylmethanamine as a yellow oil (17 mg, 28%) [M+H]$^+$: 376.

The compounds listed in Table 1 were synthesized in the same or similar manner to those described above, using appropriate commercially available starting materials and intermediates. The prepared intermediates and Examples were purified using methods well known to those skilled in the art, wherein the methods are not limited to silica gel chromatography, recrystallization, and the like. Further, the final compound obtained from the reaction mixture may be isolated as a neutral, acid or base salt.

TABLE 1

| Example No. | Compound Name | NMR Chemical Shift | HPLC Retention Time (Min) | LC-MS Value [M + H]$^+$ | Intermediate (Reaction Route) |
|---|---|---|---|---|---|
| 1 | 1-(5-(2-Fluorophenyl)-4-methoxy-1-((6-methoxypyridin-3-yl)sulfonyl)-1H-pyrrol-3-yl)-N-methylmethanamine | $^1$H NMR (400 MHz, CDCl$_3$) δ 8.12 (d, J = 2.4 Hz, 1H), 7.67-7.65 (m, 2H), 7.47-7.43 (m, 1H), 7.25 (dt, J = 7.3, 1.7 Hz, 1H), 7.18 (t, J = 7.4 Hz, 1H), 7.05 (t, J = 8.8 Hz, 1H), 6.73 (d, J = 8.8 Hz, 1H), 3.99 (s, 3H), 3.94 (s, 2H), 3.46 (s, 3H), 2.64 (s, 3H). | 9.067 | 405 | 1 (Reaction Scheme 1) |

TABLE 1-continued

| Example No. | Compound Name | NMR Chemical Shift | HPLC Retention Time (Min) | LC-MS Value [M + H]+ | Intermediate (Reaction Route) |
|---|---|---|---|---|---|
| 2 | 1-(5-(2,4-Difluorophenyl)-4-methoxy-1-((6-methoxypyridin-3-yl)sulfonyl)-1H-pyrrol-3-yl)-N-methylmethanamine | $^1$H NMR (400 MHz, CDCl$_3$) δ 8.16 (d, J = 2.4 Hz, 1H), 7.60 (dd, J = 9.0, 2.6 Hz, 1H), 7.46 (s, 1H), 7.26-7.19 (m, 1H), 6.93 (dt, J = 8.2, 1.7 Hz, 1H), 6.82 (dt, J = 9.0, 2.7 Hz, 1H), 6.73 (d, J = 9.2 Hz, 1H), 4.00 (s, 3H), 3.78 (s, 2H), 3.48 (s, 3H), 2.57 (s, 3H). | 9.495 | 423 | 3 (Reaction Scheme 1) |
| 3 | 1-(5-(2,4-Difluorophenyl)-4-methoxy-1-((6-methylpyridin-3-yl)sulfonyl)-1H-pyrrol-3-yl)-N-methylmethanamine | $^1$H NMR (400 MHz, CDCl$_3$) δ 8.44 (d, J = 2.0 Hz, 1H), 7.73 (dd, J = 8.4, 2.4 Hz, 1H), 7.60 (s, 1H), 7.22 (d, J = 8.4 Hz, 1H), 7.15 (q, J = 7.7 Hz, 1H), 6.99 (brs, 1H), 6.89 (dt, J = 8.2, 2.0 Hz, 1H), 6.80 (dt, J = 8.8, 2.4 Hz, 1H), 3.84 (s, 2H), 3.43 (s, 3H), 2.59 (s, 3H), 2.56 (s, 3H). | 8.593 | 408 | 3 (Reaction Scheme 1) |
| 4 | 1-(5-(2-Fluorophenyl)-4-methoxy-1-((6-methylpyridin-3-yl)sulfonyl)-1H-pyrrol-3-yl)-N-methylmethanamine | $^1$H NMR (400 MHz, CDCl$_3$) δ 8.42 (d, J = 2.4 Hz, 1H), 7.61 (dd, J = 8.4, 2.4 Hz, 1H), 7.34-7.12 (m, 1H), 7.37 (s, 1H), 7.23-7.13 (m, 3H), 7.04 (t, J = 8.8 Hz, 1H), 3.68 (s, 2H), 3.44 (s, 3H), 2.61 (s, 3H), 2.50 (s, 3H). | 8.453 | 390 | 2 (Reaction Scheme 2) |
| 5 | 1-(5-(2,4-Difluorophenyl)-4-methoxy-1-((6-methylpyridin-2-yl)sulfonyl)-1H-pyrrol-3-yl)-N-methylmethanamine | $^1$H NMR (400 MHz, DMSO-d$_6$) δ 7.92 (t, J = 8.0 Hz, 1H), 7.57 (d, J = 7.6 Hz, 1H), 7.39 (d, J = 7.6 Hz, 1H), 7.31 (s, 1H), 7.23-7.14 (m, 2H), 7.08-7.05 (m, 1H), 3.54 (s, 2H), 3.43 (s, 3H), 2.48 (s, 3H), 2.32 (s, 3H). | 8.793 | 407 | 3 (Reaction Scheme 1) |
| 6 | 1-(5-(2-Fluorophenyl)-4-methoxy-1-(pyridin-2-ylsulfonyl)-1H-pyrrol-3-yl)-N-methylmethanamine | $^1$H NMR (400 MHz, CDCl$_3$) δ 8.62 (dd, J = 1.6, 5.3 Hz, 1H), 7.77-7.72 (m, 1H), 7.50-7.31 (m, 4H), 7.21-7.03 (m, 2H), 6.98 (dd, J = 8.8, 8.8 Hz, 1H), 3.70-3.67 (m, 2H), 3.44 (s, 3H), 2.49 (s, 3H). | 8.407 | 376 | 2 (Reaction Scheme 2) |

In the following Test Examples, experiments were performed using any one or more of the compounds of Examples 1 to 4 according to the present disclosure.

[Test Example 1] Inhibitory Activity on Proton Pump (H$^+$/K$^+$-ATPase)

The proton pump (H+/K+-ATPase) inhibitory activity of the prepared compound was measured as follows. Gastric vesicles isolated from pig stomach were prepared according to the document (see *Methods Mol Biol.* 2016; 1377:19-27). The protein contents of the gastric vesicles were quantified with a Bicinchoninic Acid (BCA) kit (Sigma Aldrich, BCA1). To each well of a 96-well plate, 70 μl of 50 mM Tris-HEPES buffer (pH 6.5) containing 125 ng of vesicles, DMSO or a substance for each concentration (final DMSO concentration of 1%), 5 mM MgCl$_2$, and 10 mM KCl was added and pre-incubated at 37° C. for 30 minutes. Then, 10 μl of 2 mM ATP was added to each well, followed by enzymatic reaction at 37° C. for 40 minutes. The reaction was stopped by adding 20 μl of malachite green reagent (Sigma Aldrich, MAK307) and the resulting mixture was allowed to stand at room temperature for 30 minutes. By measuring the absorbance at 620 nm using a Microplate Reader (Biotek, Synergy H4), an amount of inorganic phosphorus released from ATP degradation was measured and the enzyme activity was measured. The absorbance of the enzyme-reacted sample without adding KCl was measured, and the measurement value was subtracted from all the above measurements. Assuming that the group treated with 1% DMSO (DMSO control group) was 100% H$^+$/K$^+$-ATPase enzyme activity, and that the group without KCl (KCl control group) was 0% H$^+$/K$^+$-ATPase enzyme activity, % inhibition was calculated as in the following Equation 1:

% inhibition=[1−($OD_{treatment\ group}$−$OD_{KCl\ control\ group}$)/($OD_{DMSO\ control\ group}$−$OD_{KCl\ control\ group}$)]*100.  [Equation 1]

IC$_{50}$ was obtained by nonlinear regression analysis of GraphPad Prism7 program using % inhibition values for each concentration, and results thereof are shown in Table 2 below.

TABLE 2

| Example | IC$_{50}$ (μM) |
|---|---|
| 1 | +++ |
| 2 | +++ |
| 3 | +++ |
| 4 | +++ |

(* IC$_{50}$ of 0.3 μM or less was indicated by +++)

As could be seen above, the excellent inhibitory activity of the compound according to the present disclosure on the proton pump (H$^+$/K$^+$-ATPase) was confirmed.

[Test Example 2] Inhibitory Activity and Reversibility Evaluation on Proton Pump (H$^+$/K$^+$-ATPase) Depending on pH In order to measure the change in proton pump (H$^+$/K$^+$-ATPase) inhibitory activity depending on the pH of the prepared compound, an experiment was performed in the same manner as in Test Example 1 under three conditions of pH 6.5, pH 7.0, and pH 7.5. Examples 1 and 3 were confirmed to have a higher inhibition ability in a weakly acidic condition compared to a neutral condition. It shows that the degree of inhibition ability on the gastric acid pump is better in acidic conditions, and the inhibition ability is restored after the pH in the stomach is restored.

In addition, in order to confirm the reversibility of the inhibition ability on the proton pump ($H^+/K^+$-ATPase) of the prepared compound, an experiment was performed by the jump dilution method. 6.25 μg of gastric vesicles isolated from pig stomach and 0.2 μM of each compound were pre-incubated for 120 minutes, and then the enzyme activity before dilution and the enzyme activity after 50-fold dilution were compared for each reaction time, and the reversibility was evaluated. In both Example 1 and Example 3, the inhibition ability of 50% or more was confirmed after 20 minutes of the reaction. On the other hand, when the reaction was performed for 60 minutes after the 50-fold dilution, in both Examples 1 and 3, the enzyme activity was recovered to 90% or more, and reversible results were confirmed.

Strong gastric acid suppression results in an increase in serum gastrin by a compensatory mechanism, which is highly related to the risk of hypergastrinemia, and the like.

However, the compounds of Examples 1 and 3 showed inhibitory activity by acting on the proton pump within a short time at low pH, and then showed reversibility of rapidly recovering the enzyme activity.

This shows a reversible characteristic of restoring acid secretion by easy dissociation from the proton pump, and shows low incidence of hypergastrinemia.

In other words, it could be expected from the experimental results of the present disclosure that the compounds according to the present disclosure had an excellent effect on inhibiting acid secretion without side effects on hypergastrinemia.

TABLE 3

|  | pH 6.5 | pH 7.0 | pH 7.5 |
|---|---|---|---|
| Example 1 | +++ | +++ | ++ |
| Example 3 | +++ | ++ | ++ |

(* $IC_{50}$ of 0.1 μM or less was indicated by +++ and $IC_{50}$ of greater than 0.1 μM and less than or equal to 1 μM was indicated by ++)

TABLE 4

| | % Inhibition | | | | | |
|---|---|---|---|---|---|---|
| Reaction | 20 min | | 60 min | | 120 min | |
| time | Before | After | Before | After | Before | After |
| Dilution | Dilution | Dilution | Dilution | Dilution | Dilution | Dilution |
| Example 1 | +++ | ++ | +++ | + | +++ | + |
| Example 3 | +++ | ++ | +++ | + | +++ | + |

(*% inhibition of 50% or more was indicated by +++, % inhibition of 20% or more and less than 50% was indicated by ++, and % inhibition of less than 20% was indicated by +)

[Test Example 3] Evaluation on SSTR4 Agonist Effect (cAMP Assay)

The agonism effect on SSTR4 was confirmed by cell-based cAMP functional assay. CHO cells in which human SSTR4 was stably expressed were treated with test substances for each concentration and reacted at 37° C. for 30 minutes, and an amount of the produced cAMP was measured by the HTRF detection method. The % response compared to the reference control agonist (sst-14, 10 nM) was calculated, and the $EC_{50}$ was calculated through the concentration-response curve. Results thereof are shown in Table 5 below.

TABLE 5

| Example | $EC_{50}$ (μM) |
|---|---|
| 1 | 0.78 |
| 3 | 3.9 |

As could be seen above, the compounds according to the present disclosure exhibited excellent effects as SSTR4 agonists.

[Test Example 4] Evaluation on Inhibition Ability of Basal Gastric Acid Secretion in Pylorus-Ligated Rat The inhibitory efficacy of the prepared compound on basal gastric acid secretion was measured by employing the Shay's rat model [Shay H, et al., Gastroenterology, 1945, 5, 43-61].

Male Sprague Dawley (SD) rats were divided into 8 rats per group, and fasted with only water supply for 24 hours. Then, one hour before pylorus ligation, the control group was orally administered with 0.5% methylcellulose solution, and the other groups were orally administered with the Example compound at a dose of 10 mg/10 mL/kg suspended in 0.5% methylcellulose solution.

After 5 hours of ligation, the rats were sacrificed under Zoletil and Xylazine anesthesia, and the gastric contents were enucleated by incision of the abdominal cavity. The obtained contents were centrifuged at 3,000 rpm for 10 minutes to separate only the supernatant, and gastric juice was collected. 1 mL of the collected gastric juice was taken into a beaker and the pH was measured using an electrode pH meter. To 1 mL of gastric juice, 0.03 mL each of 0.5% dimethylaminoazobenzene alcohol solution and 1% phenolphthalein alcohol solution was added to make red color, and then 0.1N NaOH solution was added, wherein the volume until the rose tint appeared was determined as the total acidity, and the total acid output was obtained by multiplying the acidity of gastric juice by the amount of gastric juice. The % inhibitory activity of the Example compound was calculated according to the following Equation 2, and results thereof are shown in Table 6 below.

% inhibitory activity of Example compound=[(total gastric acid secretion in Control group−total gastric acid secretion in group treated with Example compound)/total gastric acid secretion in Control group]×100    [Equation 2]

TABLE 6

|  | pH | Inhibitory Activity (%) |
|---|---|---|
| Vehicle Control Group | 1.74 ± 0.30 |  |
| Example 1 | 8.25 ± 0.16 | +++ |
| Example 2 | 8.04 ± 0.16 | +++ |
| Example 3 | 8.08 ± 0.24 | +++ |

90% or more: +++, 80% or more and less than 90%: ++, 70% or more and less than 80%: +

[Test Example 5] Evaluation on Gastric Acid Secretion Inhibition Ability in Lumen-Perfused Rat (LPR)

The inhibitory efficacy of the prepared compound on histamine-stimulated gastric acid secretion was measured in lumen-perfused rat (LPR) models employing Ghosh & Schild's method [Ghosh MN, et al., Br J Pharmacol Chemother., 1958, 13(1), 54~61].

A silicone tube was inserted between the stomach and esophagus of fasted male Sprague Dawley (SD) rats, and physiological saline was allowed to perfuse at the same rate. In addition, the silicone tube was inserted between the pylorus and the duodenum to allow the perfusate that had passed through the stomach to come out. Then, histamine was injected at the same rate through a syringe pump to stabilize the pH in the stomach to about 2.5. After pH stabilization, the control group was administered with only 0.5% methyl cellulose through the jugular vein or duodenum, and the PPI control group was administered with omeprazole, esomeprazole, lansoprazole, rabeprazole, or the like. The other groups were injected with the Example compound by the same route. The perfusate was collected by 7.5 mL aliquots every 15 minutes after drug administration and the pH was measured.

[Test Example 6] Evaluation on Gastric Damage Inhibitory Efficacy in Rat of Indomethacin-Induced Gastric Damage The experiment was performed as follows to evaluate the gastric ulcer inhibitory efficacy of the Example compound in rat models of gastric damage induced by indomethacin, a drug in the NSAID classes.

Among fasted male Sprague Dawley rats, the control group was orally administered with 0.5% methylcellulose solution, and the other groups were orally administered with the Example compound at a dose of 10 mg/10 mL/kg suspended in 0.5% methylcellulose solution.

In 1 hour after oral administration of the Example compound, indomethacin was orally administered, and after 5 hours, the test animals were sacrificed and the stomach was enucleated. After washing the enucleated surface of the stomach, the greater curvature of the stomach was incised. The incised stomach was spread out and fixed. Then, the ratio of the gastric damaged area was obtained by the total gastric area and the damaged area on the gastric mucosa surface using ImageJ software (NIH, Bethesda), and the % inhibitory activity of the Example compound was calculated according to the following Equation 3. Results thereof are shown in Table 7 below:

% inhibitory activity of Example compound=[(ratio of gastric damaged area in control group−ratio of gastric damaged area in group treated with Example compound)/(ratio of gastric damaged area in control group)]×100   [Equation 3]

TABLE 7

| | Inhibitory Activity (%) |
|---|---|
| Dose | 10 mg/kg |
| Example 1 | +++ |
| Example 3 | +++ |

97% or more: +++, 90% or more and less than 97%: ++, 80% or more and less than 90%: +

[Test Example 7] Efficacy Evaluation for Ethanol-Induced Gastric Damage and Gastrointestinal Inflammatory Disease Alcohol may directly cause damage and bleeding to the gastric mucosal layer, and indirectly promotes the secretion of inflammatory cytokines, lipopolysaccharides, endotoxins, or free radicals through infiltration of macrophages and neutrophils, causing both gastric ulcer and gastrointestinal inflammation. The following experiment was performed to evaluate the gastric ulcer inhibitory efficacy and gastrointestinal anti-inflammatory efficacy of the Example compound in rat models of alcohol-induced gastric damage and gastrointestinal inflammatory disease.

Among fasted male Sprague Dawley rats, the control group was orally administered with 0.5% methylcellulose solution, and the other groups were orally administered with the Example compound suspended in 0.5% methylcellulose solution.

In 1 hour after oral administration of the Example compound, the test animals were orally administered with 100% ethanol, anesthetized 1 hour later, and was subjected to laparotomy to collect blood from the posterior vena cava. The blood was allowed to stand at room temperature for about 15 minutes to coagulate, and then centrifuged to separate the serum. After completion of blood collection, the stomach was enucleated. After washing the surface of the enucleated stomach with physiological saline, the greater curvature of the stomach was incised. The incised stomach was placed on a fixture, spread out using forceps, and fixed with a fixing pin. Then, the total gastric area and the damaged area on the gastric mucosa surface were analyzed using ImageJ software (NIH, Bethesda). The gastric tissue was homogenized and centrifuged to obtain gastric tissue protein from the supernatant, and the inflammatory cytokine concentration in the gastric tissue was measured. The inflammatory cytokine concentration in the blood in the isolated serum were measured by enzyme-linked immunosorbent assay (ELISA) technique.

[Test Example 8] Efficacy Evaluation for Acid Reflux-Induced Reflux Esophagitis

The following experiment was performed to evaluate the esophageal damage inhibitory efficacy of the Example compound in rats with acid reflux-induced reflux esophagitis.

Among fasted male Sprague Dawley rats, the control group was orally administered with 0.5% methylcellulose solution, and the other groups were orally administered with the Example compound suspended in 0.5% methylcellulose solution.

In 1 hour after oral administration of the Example compound, the test animals were anesthetized and was subjected to laparotomy. The pylorus of the stomach and the boundary between the proximal stomach and the body were further ligated to allow gastric acid to reflux into the esophagus. After a predetermined period of time, the stomach and esophagus of the test animals were carefully enucleated, the gastric contents were collected and gastric juice was taken, and the pH and amount of gastric juice were measured. The enucleated esophagus was incised in the longitudinal direction and fixed to expose the mucosal area. Esophageal damaged area was analyzed using ImageJ software (NIH, Bethesda).

[Test Example 9] Efficacy Evaluation on Mepirizole-Induced Duodenal Damage

The experiment was performed as follows to evaluate the duodenal ulcer inhibitory efficacy of the Example compound in rat models of duodenal damage induced by mepirizole, a drug in the NSAID classes.

Among male Sprague Dawley rats, the control group was orally administered with 0.5% methylcellulose solution, and the other groups were orally administered with the Example compound suspended in 0.5% methylcellulose solution.

In 1 hour after oral administration of the Example compound, mepirizole was orally administered, and after a predetermined period of time, the test animals were sacrificed and the duodenum was enucleated. After washing the surface of the enucleated duodenum with physiological saline, the damaged area was analyzed using ImageJ software (NIH, Bethesda).

[Test Example 10] Measurement of Change in Gastrin in Blood after Administration of Example Compound The experiment was performed as follows to observe the change in gastrin in the blood after administration of the Example compound according to the present disclosure.

Among fasted male Sprague Dawley rats, the control group was orally administered with 0.5% methylcellulose solution, and the other groups were orally administered with the Example compound suspended in 0.5% methylcellulose solution.

About 0.5 mL of blood was collected from the jugular vein of the test animals in 5 hours, 8 hours, 12 hours or 24 hours after oral administration of the Example compound.

The gastrin concentration in the blood was measured using the ELISA technique in the collected blood.

[Test Example 11] Evaluation on Anti-Inflammatory Efficacy on Indomethacin-Induced Small Intestinal Inflammation The following experiment was performed to measure the inflammatory change after administration of the Example compound in rats of small intestinal inflammation induced by indomethacin, a drug in the NSAID classes.

Among male C57BL/6 mice or male Sprague Dawley rats, the control group was intraperitoneally administered with 0.5% methylcellulose solution, and the other groups were intraperitoneally administered with the Example compound suspended in 0.5% methylcellulose solution daily for a predetermined period of time. Indomethacin was orally administered on the last day of administration of the Example compound to induce small intestinal inflammation.

After a predetermined period of time, the test animals were sacrificed and the small intestine was enucleated. After washing the surface of the enucleated small intestine with physiological saline, damage to the small intestine such as bleeding and inflammation, or the like, was analyzed through histological analysis. The enucleated small intestine tissue was homogenized and centrifuged, and then total RNA was obtained from the small intestine tissue in the supernatant, and an amount of inflammatory cytokine mRNA in the small intestine tissue was measured.

[Test Example 12] Gastrointestinal Neuroendocrine Tumor Observation after Long-Term Administration of Example Compound The following experiment was performed to observe the degree of gastrointestinal neuroendocrine tumors caused by changes in gastrin secretion after long-term administration of the Example compound.

Among Sprague Dawley rats, the control group was orally administered with 0.5% methylcellulose solution, and the other groups were orally administered with a high dose of the Example compound suspended in 0.5% methylcellulose solution daily for 2 years. After a predetermined period of time, the test animals were sacrificed, the stomach and duodenum were enucleated and fixed. Then, the degree of hyperplasia of ECL cells and the incidence of neuroendocrine tumors were observed by histopathological analysis, and compared with the control group.

[Test Example 13] Intragastric Distribution Test

After oral administration of the Example compound in normal rats, the intragastric distribution by time was measured as follows. The prepared compound was dissolved in distilled water containing 0.5% methylcellulose to 0.2 mg/mL, and then orally administered at a dosage of 4 mg/kg. Rats were sacrificed at 1 hour, 6 hours, 12 hours, and 24 hours after administration. Then, blood was exsanguinated through the heart and perfused with physiological saline, the gastric tissue was enucleated, weighed, and stored at $-80°$ C. until the point of analysis. PBS buffer was added so that the ratio of gastric tissue weight to PBS buffer was 1:4, and the compound in gastric tissue was extracted using a homogenizer. The supernatant of the extract was taken and was subjected to protein precipitation using acetonitrile, and then an amount of the Example compound was measured using LC-MS/MS.

The calculated exposure in the stomach $AUC_{last}$, stomach is shown in Table 8 below. Example 1 showed an excellent intragastric distribution, and the concentration in the stomach exceeded ICH of the in vitro $H^+/K^+$ ATPase inhibition assay at all time points.

TABLE 8

| $AUC_{last,stomach}$ obtained after a single administration of the compound of Example 1 at a dose of 4 mg/kg $AUC_{last,stomach}$ (nmol/kg tissue * hr) | |
|---|---|
| Compound | Example 1 |
| $AUC_{last,stomach}$ | 171,252 |

It was confirmed from the above results that the compounds according to the present disclosure had excellent intragastric distribution effect.

[Test Example 14] Pharmacokinetic Test in Rats and Beagle Dogs

The Example compound was dissolved in PBS containing 5% DMSO and 20% hydroxypropyl (HP) beta cyclodextrin, and administered intravenously to rats at a dose of 5 mg/kg, and the Example compound was suspended in distilled water containing 0.5% methylcellulose, and orally administered to rats at a dose of 10 mg/kg. The Example compound was dissolved in PBS containing 5% DMSO and 20% hydroxypropyl (HP) beta cyclodextrin, and administered intravenously to beagle dogs at a dose of 5 mg/kg, and the Example compound was suspended in distilled water containing 0.5% methylcellulose, and orally administered to beagle dogs at a dose of 10 mg/kg. Blood samples were collected at scheduled time points after the single intravenous and oral administration of the Example compound to normal rats and beagle dogs. Acetonitrile containing an internal standard material was added to the collected blood sample for protein precipitation. The sample extracted through protein precipitation was centrifuged, and then the supernatant was injected into LC-MS/MS to be subjected to quantitative analysis of the blood concentration of the Example compound. The AUC for each administration route was calculated based on the blood concentration-time profile obtained as a result above, and based on this, the bioavailability (F) upon oral administration was calculated.

Results thereof are shown in Tables 9 and 10.

TABLE 9

Pharmacokinetic parameters calculated after single oral administration of Example compounds to rats
In vivo Rat PO PK Parameters

| Compound | Oral Dose (mg/kg) | $AUC_{inf}$ (ng * hr/mL) | F (%) |
| --- | --- | --- | --- |
| Example 1 | 10 | 252.8 | 22.0 |
| Example 3 | 10 | 275.4 | 27.3 |

TABLE 10

Pharmacokinetic parameters calculated after single administration of Example compound to beagle dogs
In vivo Dog PO PK Parameters

| Compound | Oral Dose (mg/kg) | $AUC_{inf}$ (ng * hr/mL) | F (%) |
| --- | --- | --- | --- |
| Example 1 | 10 | 10176.3 | 71.7 |
| Example 3 | 10 | 14455.4 | 83.8 |

As could be seen in Tables 9 and 10, the compound according to the present disclosure had very excellent bioavailability (F) upon oral administration to exhibit remarkably excellent effect in view of pharmacokinetics.

In the present specification, the detailed description of the contents that are able to be sufficiently recognized and inferred by those skilled in the art of the present disclosure has been omitted. In addition to the specific examples described in the present specification, various modifications can be made within the scope that does not change the technical spirit or essential configuration of the present disclosure. Therefore, the present disclosure may be practiced in a manner different from that specifically described and exemplified in the present specification, which can be understood by those skilled in the technical field of the present disclosure.

What is claimed is:

1. A compound represented by the following Chemical Formula 2 or a pharmaceutically acceptable salt thereof:

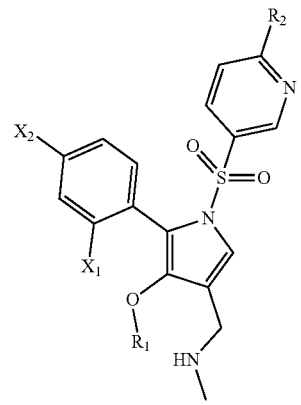

[Chemical Formula 2]

in the Chemical Formula 2,
$X_1$ is F;
$X_2$ is hydrogen or F;
$R_1$ is methyl; and
$R_2$ is methoxy, ethoxy, methyl or ethyl.

2. The compound, or the pharmaceutically acceptable salt thereof of claim 1, wherein $R_2$ is methoxy or methyl.

3. The compound, or the pharmaceutically acceptable salt thereof of claim 1,
wherein $R_1$ is methyl, and
$R_2$ is methoxy or methyl.

4. The compound, or the pharmaceutically acceptable salt thereof of claim 1,
wherein
$X_1$ is F;
$X_2$ is F;
$R_1$ is methyl; and
$R_2$ is methoxy or methyl.

5. The compound, or the pharmaceutically acceptable salt thereof of claim 1,
wherein
$X_1$ is F;
$X_2$ is hydrogen;
$R_1$ is methyl; and
$R_2$ is methoxy or methyl.

6. The compound, or the pharmaceutically acceptable salt thereof of claim 1,
wherein
$X_1$ is F;
$X_2$ is hydrogen or F;
$R_1$ is methyl; and
$R_2$ is methoxy.

7. The compound, or the pharmaceutically acceptable salt thereof of claim 1, wherein
$X_1$ is F;
$X_2$ is hydrogen or F;
$R_1$ is methyl; and
$R_2$ is methyl.

8. The compound, or the pharmaceutically acceptable salt thereof of claim 1, wherein the compound represented by Chemical Formula 2 is any one selected from the group consisting of the following compounds:
1-(5-(2-fluorophenyl)-4-methoxy-1-((6-methoxypyridin-3-yl)sulfonyl)-1H-pyrrol-3-yl)-N-methylmethanamine;
1-(5-(2,4-difluorophenyl)-4-methoxy-1-((6-methoxypyridin-3-yl)sulfonyl)-1H-pyrrol-3-yl)-N-methylmethanamine;

1-(5-(2,4-difluorophenyl)-4-methoxy-1-((6-methylpyridin-3-yl)sulfonyl)-1H-pyrrol-3-yl)-N-methylmethanamine; and 1-(5-(2-fluorophenyl)-4-methoxy-1-((6-methylpyridin-3-yl)sulfonyl)-1H-pyrrol-3-yl)-N-methylmethanamine.

9. A pharmaceutical composition for preventing or treating gastrointestinal ulcers, gastrointestinal inflammatory diseases, or gastric acid-related diseases, comprising the compound according to any one of claims 1 to 8 or the pharmaceutically acceptable salt thereof, wherein the gastrointestinal ulcer, gastrointestinal inflammatory disease or gastric acid-related disease is any one or more selected from the group consisting of peptic ulcer, gastric ulcer, duodenal ulcer, NSAID-induced ulcer, acute stress ulcer, Zollinger-Ellison syndrome, *Helicobacter pylori* infection, gastritis, erosive esophagitis, non-erosive esophagitis, reflux esophagitis, inflammatory bowel disease, symptomatic gastroesophageal reflux disease (symptomatic GERD), functional dyspepsia, gastric cancer, gastric MALT lymphoma, hyperacidity, and upper gastrointestinal hemorrhage due to invasive stress.

\* \* \* \* \*